United States Patent
Blackwell et al.

(10) Patent No.: US 7,896,923 B2
(45) Date of Patent: Mar. 1, 2011

(54) ARTHROSCOPIC UNICOMPARTMENTAL KNEE IMPLANTATION SYSTEM AND RELATED METHOD

(75) Inventors: Timothy J Blackwell, Davie, FL (US); Jacy C Hoeppner, Warsaw, IN (US); John A Repicci, Buffalo, NY (US)

(73) Assignee: Biomet Manufacturing Corp., Warsaw, IN (US)

( * ) Notice: Subject to any disclaimer, the term of this patent is extended or adjusted under 35 U.S.C. 154(b) by 131 days.

(21) Appl. No.: 11/607,109

(22) Filed: Nov. 30, 2006

(65) Prior Publication Data

US 2008/0133020 A1 Jun. 5, 2008

(51) Int. Cl.
*A61F 2/38* (2006.01)

(52) U.S. Cl. .................. 623/20.21; 623/20.3; 623/20.32; 623/20.35

(58) Field of Classification Search ............... 623/14.12, 623/20.21, 20.14–20.17, 20.3–20.36, 23.5, 623/22.35–22.37; 606/266, 287, 291, 307
See application file for complete search history.

(56) References Cited

U.S. PATENT DOCUMENTS

| | | | |
|---|---|---|---|
| 3,852,830 A | | 12/1974 | Marmor |
| 3,958,278 A | * | 5/1976 | Lee et al. .................. 623/20.21 |
| 4,034,418 A | | 7/1977 | Jackson et al. |
| 4,355,429 A | * | 10/1982 | Mittelmeier et al. ...... 623/20.14 |
| 4,865,607 A | * | 9/1989 | Witzel et al. ............... 623/20.32 |
| 4,919,671 A | | 4/1990 | Karpf et al. |
| 5,486,180 A | | 1/1996 | Dietz et al. |
| 5,549,683 A | * | 8/1996 | Bonutti ...................... 623/20.33 |
| 5,888,204 A | * | 3/1999 | Ralph et al. ................ 623/22.36 |
| 6,364,910 B1 | | 4/2002 | Shultz et al. |
| 6,494,914 B2 | * | 12/2002 | Brown et al. ................ 623/20.3 |
| 6,503,280 B2 | | 1/2003 | Repicci |
| 6,520,964 B2 | * | 2/2003 | Tallarida et al. ............... 606/71 |
| 6,554,866 B1 | | 4/2003 | Aicher et al. |
| 2003/0100953 A1 | | 5/2003 | Rosa et al. |
| 2005/0143831 A1 | * | 6/2005 | Justin et al. ................ 623/20.17 |
| 2005/0148231 A1 | | 7/2005 | Riester et al. |
| 2006/0004461 A1 | | 1/2006 | Justin et al. |
| 2006/0009855 A1 | * | 1/2006 | Goble et al. ............... 623/20.15 |
| 2006/0020344 A1 | | 1/2006 | Shultz et al. |

(Continued)

FOREIGN PATENT DOCUMENTS

DE 3136636 3/1983

(Continued)

OTHER PUBLICATIONS

Biomet® Orthopedics, Inc., "repicci II® Unicondylar Program, Surgical Technique featuring the PowerMill™ System from MicroAire® Surgical Instruments", brochure, Jul. 2004 (20 pages).

(Continued)

*Primary Examiner* — David H Willse
*Assistant Examiner* — Megan Wolf
(74) *Attorney, Agent, or Firm* — Harness, Dickey

(57) ABSTRACT

A knee implantation system for replacing a portion of a knee joint includes an unicondyler tibial implant configured to replace a portion of a tibia that includes a first member and a second member. The first member has a body portion that includes an articulating surface for replacing only a single superior articulating surface of the tibia. The second member has a textured surface. The second member is removably connected to the body portion and the textured surface is disposed about opposite the articulating surface.

21 Claims, 21 Drawing Sheets

U.S. PATENT DOCUMENTS

2007/0233268 A1* 10/2007 Wagner et al. ............. 623/20.14

FOREIGN PATENT DOCUMENTS

| EP | 0151724 | 8/1985 |
| EP | 0170779 | 2/1986 |
| EP | 0809986 | 12/1997 |
| FR | 2575920 | 7/1986 |
| FR | 2836821 | 9/2003 |

OTHER PUBLICATIONS

Hart, John A., Fracs, FAOrthA, FACSP(Hon), Clinical Associate Professor, Department of Surgery, Monash University, Melbourne, VIC., "Joint Replacement Surgery", Bone and Joint Disorders: Prevention and Control, MJA vol. 180, Mar. 2004, pp. S27-S30.

Partial European Search Report mailed Mar. 18, 2008 for European Patent Application No. 07254638.5.

European Search Report mailed Jun. 3, 2008 for European Patent Application No. 07254638.5.

* cited by examiner

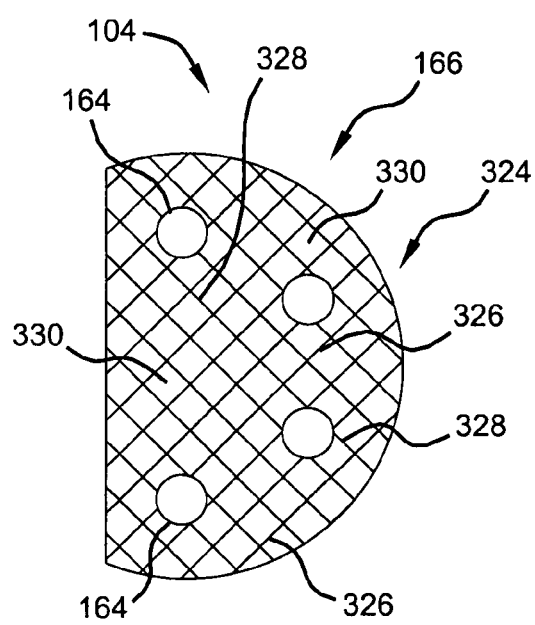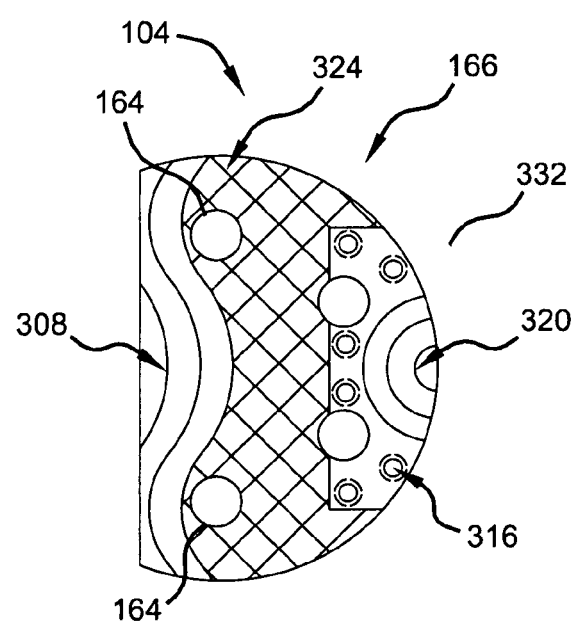
Figure 14I
Figure 14J

ARTHROSCOPIC UNICOMPARTMENTAL KNEE IMPLANTATION SYSTEM AND RELATED METHOD

FIELD

The present teachings relate to a medical prosthetic and more particularly relate to a unicompartmental knee prosthetic system and related method.

BACKGROUND

With reference to FIGS. 1 and 2, a human knee joint is shown and generally indicated by reference numeral 10. The knee joint 10 includes a femur 12, a tibia 14, a fibula 16 and a patella 18. A myriad of medical problems can require partial or complete replacement of one or more portions of the aforesaid bones. In previous medical procedures, relatively large and complex prosthetics may be passed through one or more incisions and couple to the respective bones. The prosthetics may require relatively larger incisions and relatively complex manipulation to insert and secure the prosthetics to the bone.

The relatively larger incisions and complex manipulation of the prosthetics may require additional movement and/or cutting of the soft tissue surrounding the knee joint 10. The additional movement and/or cutting of the soft tissue may cause longer recovery times and additional trauma to the knee joint 10.

SUMMARY

The present teachings generally include a knee implantation system for replacing a portion of a knee joint. The knee implantation system includes an unicondyler tibial implant configured to replace a portion of a tibia that includes a first member and a second member. The first member has a body portion that includes an articulating surface for replacing only a single superior articulating surface of the tibia. The second member has a textured surface. The second member is removably connected to the body portion and the textured surface is disposed about opposite the articulating surface.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present teachings.

FIG. 3 also illustrates reference planes with respect to the knee joint.

FIG. 10A also shows the configuration of the locking mechanism relative to the bone screw.

DETAILED DESCRIPTION

The following description of the various aspects of the present teachings is merely exemplary in nature and is in no way intended to limit the teachings. While the various illustrated aspects of the present teachings pertain to a knee joint 10 of the human body, it will be appreciated that the teachings may also be applicable to various bones of the human body including, but not limited to, the tibia, the fibula, the humerus, the ulna or the radius. It will also be appreciated that the teachings may be applicable to various bones of other animals, mammalian or otherwise, requiring replacement with prosthetics due to various medical concerns.

Figure 4:
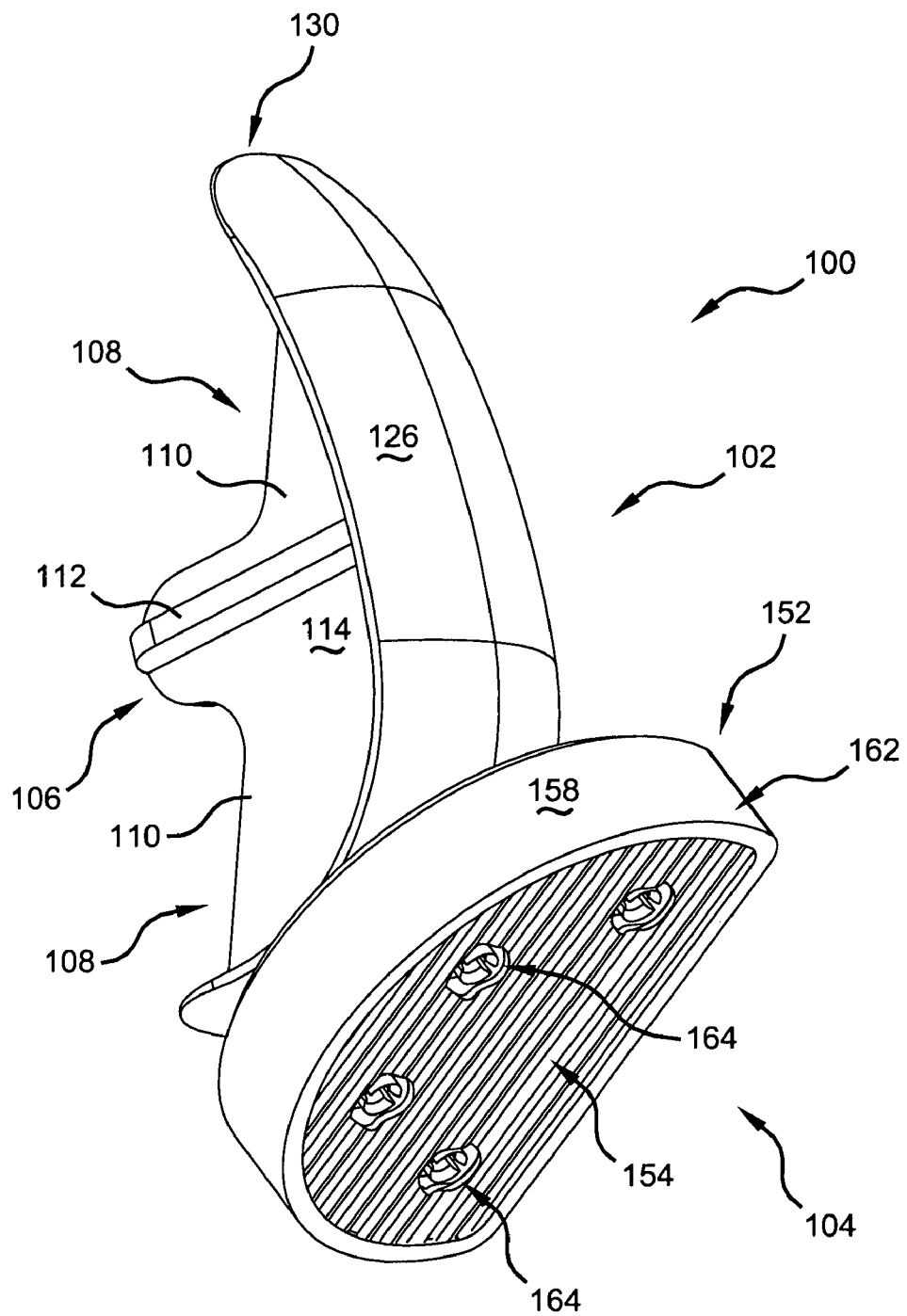
FIG. 4 is a perspective view of a portion of an exemplary unicompartmental knee implant system constructed prosthetic in accordance with the present teachings showing a femoral component and a tibial component.

With reference to FIG. 4 and in accordance with the present teachings, a unicompartmental knee implantation system 100 generally can include a femoral component 102 and a tibial component 104. The femoral component 102 can include a peg 106 and a wall 108 that can intersect, abut and/or be integrally formed with the peg 106. The wall 108 can include a web keel 110. The wall 108 can also include a cross-web keel 112, which can be generally perpendicular to the web keel 110. The peg 106 can generally extend from a center 114 of the femoral component 102. The cross-web keel 112 and a portion of the web keel 110 (i.e., the portion adjacent to the cross-web keel 112) can define the peg 106. In another aspect, the wall 108 of the femoral component 102 can intersect and/or abut the peg 106, e.g., a multiple component construction where the peg 106 is separate from the wall 108.

The femoral component 102 can be made of a cobalt chrome alloy, one or more other suitable bio-compatible materials and/or a suitable combination of materials. The femoral component 102 can also be coated (partially or entirely) in a titanium plasma coating. The titanium plasma coating can be sputter-coated onto a portion of the (or the entire) femoral component 102. It may be shown that the titanium plasma coating can create a porous surface on the femoral component 102 that can promote bone growth thereto.

Figure 5:
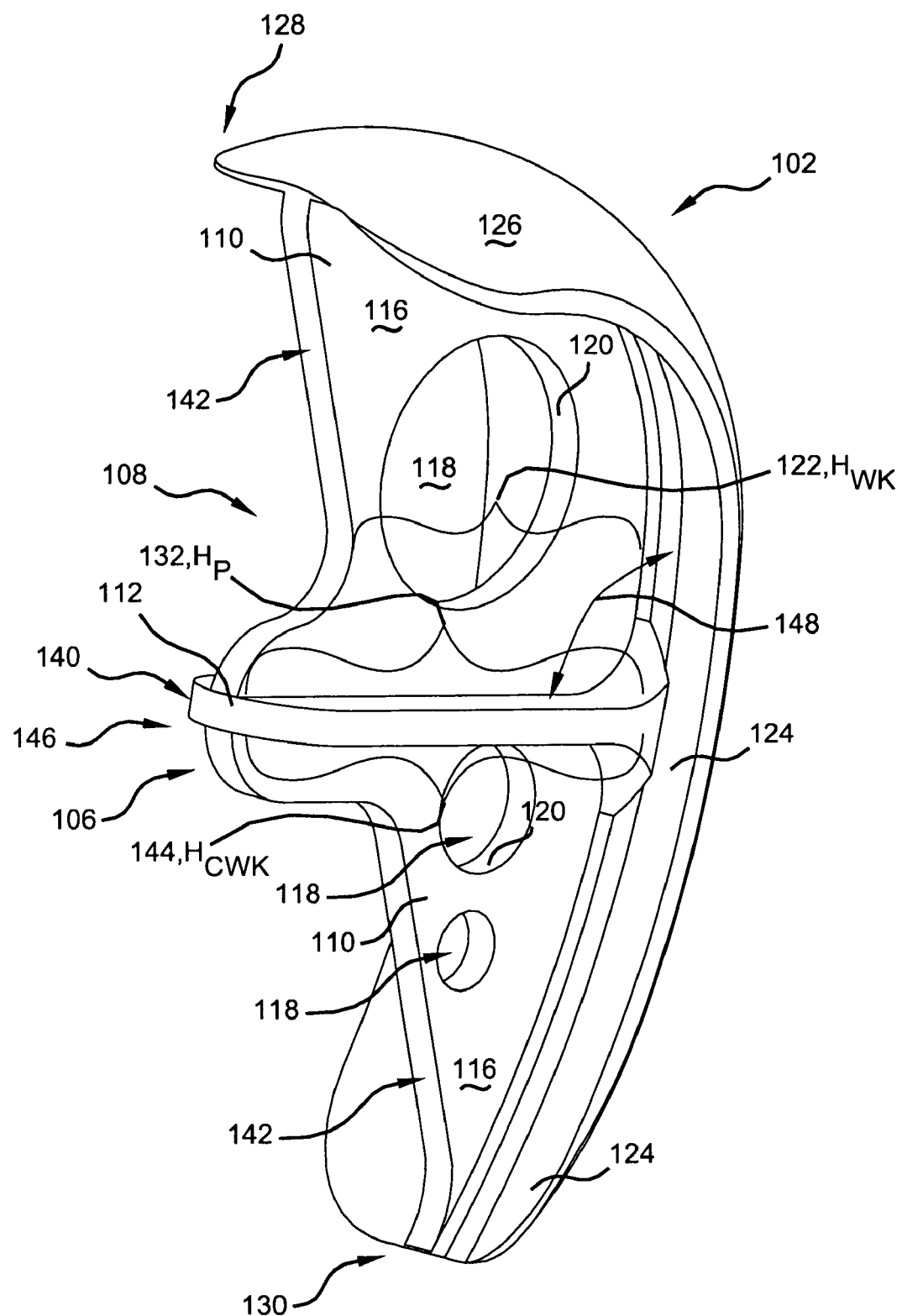
FIG. 5 is a perspective view of the femoral component of FIG. 4 showing bone in-growth holes in a web keel.
Figure 12A:
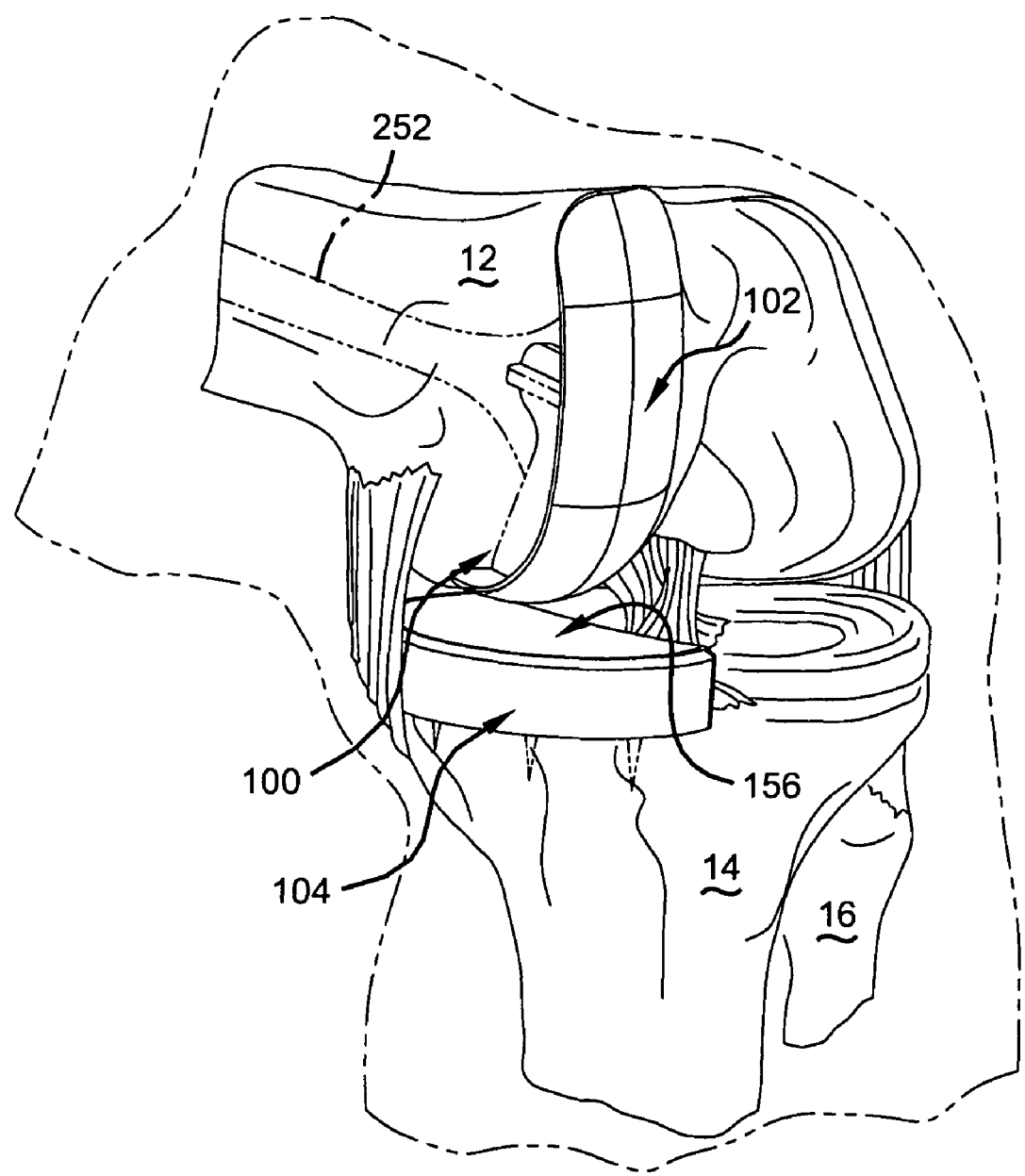
FIG. 12A is a perspective view of a knee showing a femoral component secured to the medial condyle and a tibial component secured to the medial articular surface of the tibia in accordance with the present teachings.
Figure 12B:
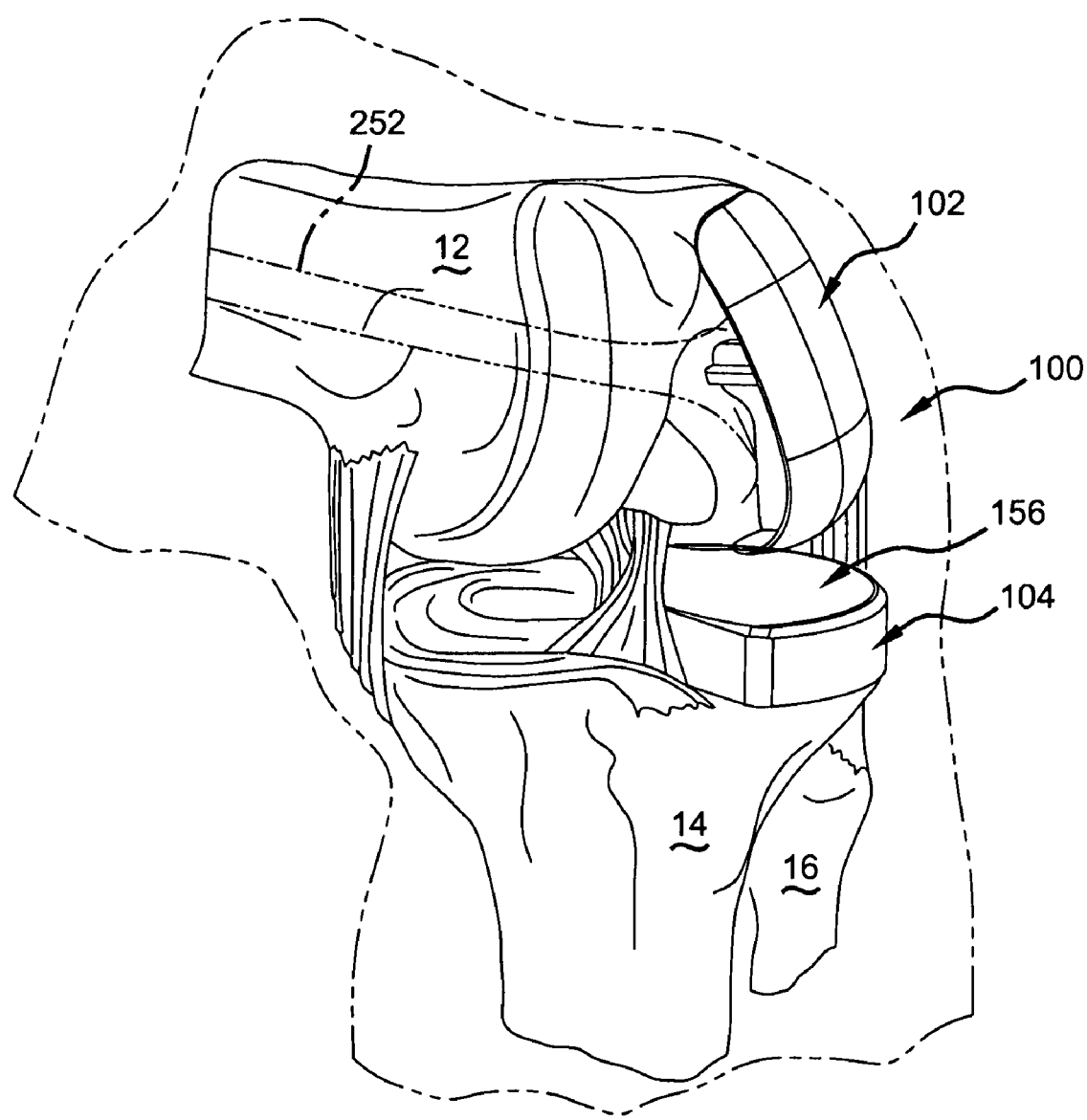
FIG. 12B is similar to FIG. 12A and shows a femoral component secured to the lateral condyle and a tibial component implanted over the lateral articular surface of the tibia.

With reference to FIG. 5, the web keel 110 and/or the cross-web keel 112 can have a web portion 116 that can define one or more holes 118 formed (entirely or partially) therethrough. The holes 118 through the web keel 110 and/or the cross-web keel 112 can promote bone growth therethrough (or therein) after the femoral component 102 has been implanted in the femur 12, as is illustrated in FIGS. 12A and 12B. The plurality of holes 118 can be formed as circles, rectangles or other polygonal shapes. When the plurality of holes 118 are not formed entirely through the web portion 116, dimples, depressions, waves and/or other suitable structures, shapes, configurations, etc. can be formed on the web keel 110 and/or the cross-web keel 112. An edge 120 of each of the plurality of holes 118 can be chamfered, dimpled, scalloped, rounded and/or various combinations thereof and, as such, can promote bone growth therethrough (or therein). The titanium plasma coating can be applied on the web portion 116 (partially or entirely) and/or can be applied near the holes 118 and/or the edge 120.

Figure 6:
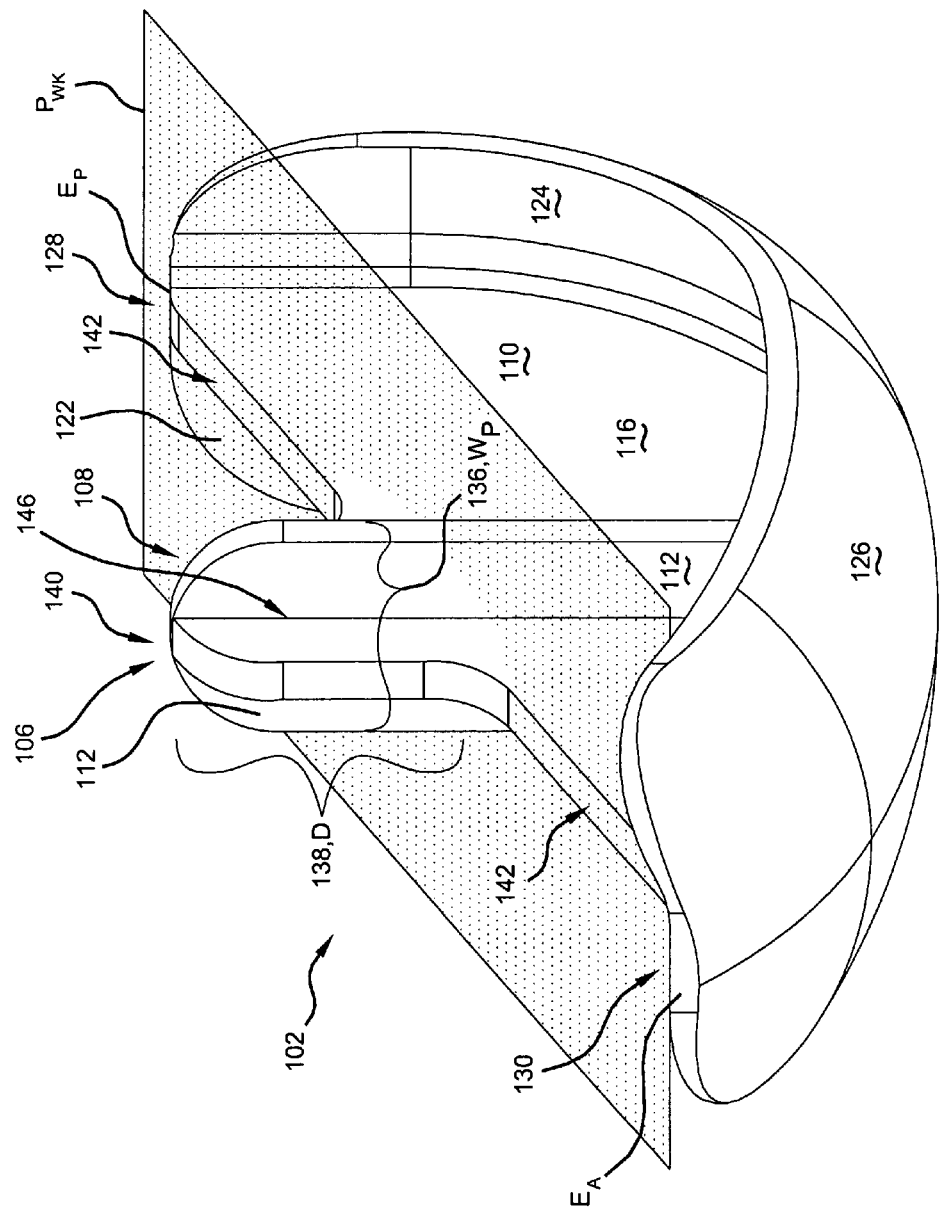
FIG. 6 is similar to FIG. 4 and shows a height and a width of a peg relative to the web keel but does not show bone in-growth holes.

With reference to FIGS. 5 and 6, the web keel 110 can have a dimension that can define a height 122 (i.e., $H_{wk}$ shown in FIG. 5) from a rear face 124 of the femoral component 102. The rear face 124 can be generally opposite an articulating surface 126. The height 122 ($H_{WK}$) of the web keel 110 can vary such that the web keel 110 can be about flush (i.e., contoured to join) with the rear face 124 near a posterior side 128 and/or an anterior side 130 of the femoral component 102. The height 122 ($H_{WK}$) of the web keel 110 adjacent the peg 106 can be almost equal to a height 132 of the peg 106 (i.e., $H_P$ as shown in FIG. 5).

It may be shown that the varying height 122 ($H_{WK}$) of the web keel 110 and/or the relatively little difference between the height 132 ($H_P$) of the peg 106 and the height 122 ($H_{WK}$) of the web keel 110 can be shown to make insertion of the femoral component 102 through the incision 134 (FIG. 3) relatively easier. This may be so because of the possible reduction of the propensity of catching or hanging up the femoral component 102 on the incision 134 and/or other medical equipment, including, but not limited to, an interior surface of a cannula.

The height 122 ($H_{WK}$) of the web keel 110 can be based on the height 132 ($H_P$) (FIG. 5) and/or a dimension defining a width 136 (i.e., $W_P$) (or diameter if applicable) of the peg 106, as shown in FIG. 6. A dimension 138 (i.e., D) can define a difference in a value of the length between a top 140 of the peg 106 and a top edge 142 of the web keel 110 adjacent to the peg 106, i.e., (D), is about equal to ($H_P$) minus ($H_{WK}$). The dimension 138 (D) can be less than or generally equal to the width 136 (or diameter) of the peg 106 ($W_P$) (i.e., D about $\leq W_P$). In another aspect, the height 122 ($H_{WK}$) of the web keel 110 adjacent to the peg 106 can be greater than or generally equal to a value of the height 132 ($H_P$) of the peg 106 minus the width 136 (or diameter) ($W_P$) of the peg 106. In addition, the height 122 ($H_{wk}$) of the web keel 110 adjacent to the peg 106 can be less than or generally equal to the height 132 ($H_P$) of the peg 106 (i.e., $H_P$ about $\geq H_{WK}$ about $\geq H_P - H_{WK}$).

In further aspects of the present teachings, the height (HWK) of the web keel 110 can be predetermined by need not based on the height 132 (Hp) and/or the width 136 (Wp) of the peg 106, notwithstanding, the peg 106 can have a varying width, diameter and/or taper. With reference to FIG. 6, an imaginary plane (PWK) can extend between the posterior side 128 and the anterior side 130 of the femoral component 102. The imaginary plane (PWK) can contact the posterior side 128 where the rear face 124 and the articulating surface 126 can terminate at a posterior edge (EP). The imaginary plane (PWK) can also contact the rear face 124 of the anterior side 130 near an anterior edge (EA). It will be appreciated that the imaginary plane (PWK) can contact either edge or contact near either edge (EP, EA) of the femoral component 102. Specifically, as shown in the embodiments of FIGS. 5 and 6, the imaginary plane PWK can intersect the articulating surface 126 adjacent the anterior side 130. Also, the imaginary plane PWK can be spaced apart at a distance from the articulating surface 126 adjacent the posterior side 128 to be in a non-intersecting relationship with the articulating surface 126 adjacent the posterior side 128.

The web keel 110 can extend from the rear face 124 substantially to the imaginary plane ($P_{WK}$). In this regard, the web keel 110 can abut the imaginary plane ($P_{WK}$) or can be spaced therefrom to accommodate, for example, curvature in the web keel 110. As such, the web keel 110 need not be completely flush with the imaginary plane ($P_{WK}$). In other aspects, the peg 106 can extend through the imaginary plane ($P_{WK}$). In this regard, portions of the web keel 110 can be contoured to join the peg 106 and, therefore, portions of the web keel 110 can extend beyond the imaginary plane ($P_{WK}$). The cross-web keel 112 can also extend beyond the imaginary plane ($P_{WK}$) and can be contoured to join the peg 106.

With reference to FIG. 5, a dimension can define a height 144 of the cross-web keel 112 (i.e., $H_{CWK}$). The height 144 ($H_{CWK}$) can be less than or generally equal to the height 132 ($H_P$) of the peg 106 (i.e., $H_{CWK}$ about $\leq H_P$). The top 140 of the peg 106 can be contoured to join the web keel 110 and/or the cross-web keel 112. Intersections 146 between the web keel 110 and the cross-web keel 112 can be rounded and/or chamfered (i.e., no sharp outside/inside corners and/or rounded edges). It may be shown that doing so can reduce the propensity of catching or hanging up the femoral component 102 on the incision 134 (FIG. 3) and/or other suitable medical equipment (e.g., an interior of a cannula.)

Figures 1, 2:
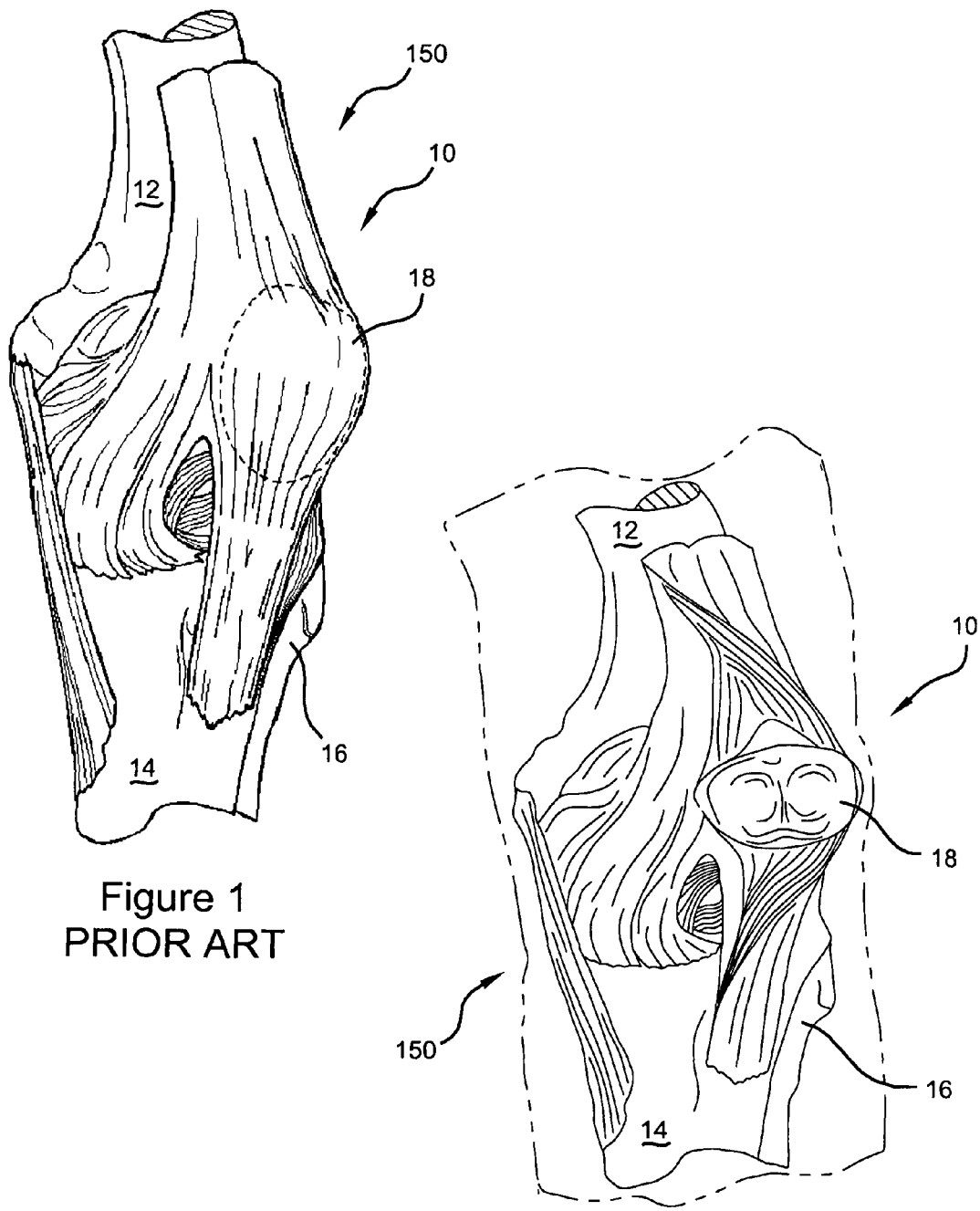
FIG. 1 is a prior art front view of a knee joint showing bones, muscle tissue and connective tissue of the knee joint.
FIG. 2 is similar to FIG. 1 and shows a patella, associated muscles and connective tissue partially separated from the respective portions of the knee joint.
Figure 3:
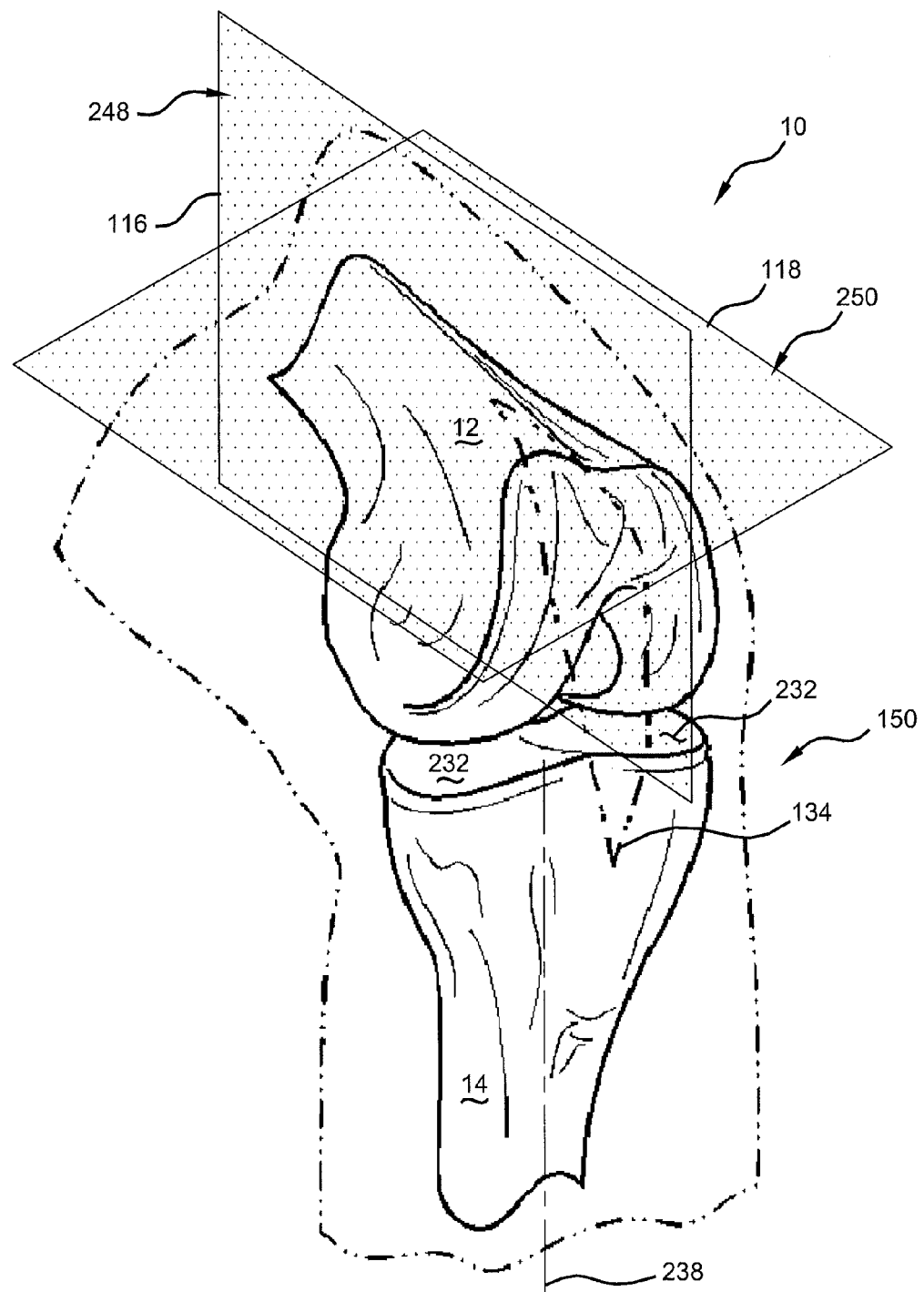
FIG. 3 is a perspective view of the knee joint, absent the muscle and connective tissue, showing a lateral condyle and a medial condyle of the femur and an exemplary incision in accordance with the present teachings.

A predetermined orientation of the peg 106 relative to the rear face 124 (e.g., an angle formed therebetween) can be shown to reduce the catching or hanging up the femoral component 102 on the incision 134 (FIG. 3) and/or other suitable medical equipment. As such, the peg 106 can extend from the rear face 124 in a direction that can be generally perpendicular to the rear face 124. The peg 106 can also be positioned such that an angle 148 (FIG. 5) defined between the peg 106 and the rear face 124 can be less than 90 degrees. The angle 148 of the peg 106 relative to the rear face 124 can be varied so that the predetermined angle can further facilitate compatibility with a native bone structure 150 (FIGS. 1-3).

Figure 7:
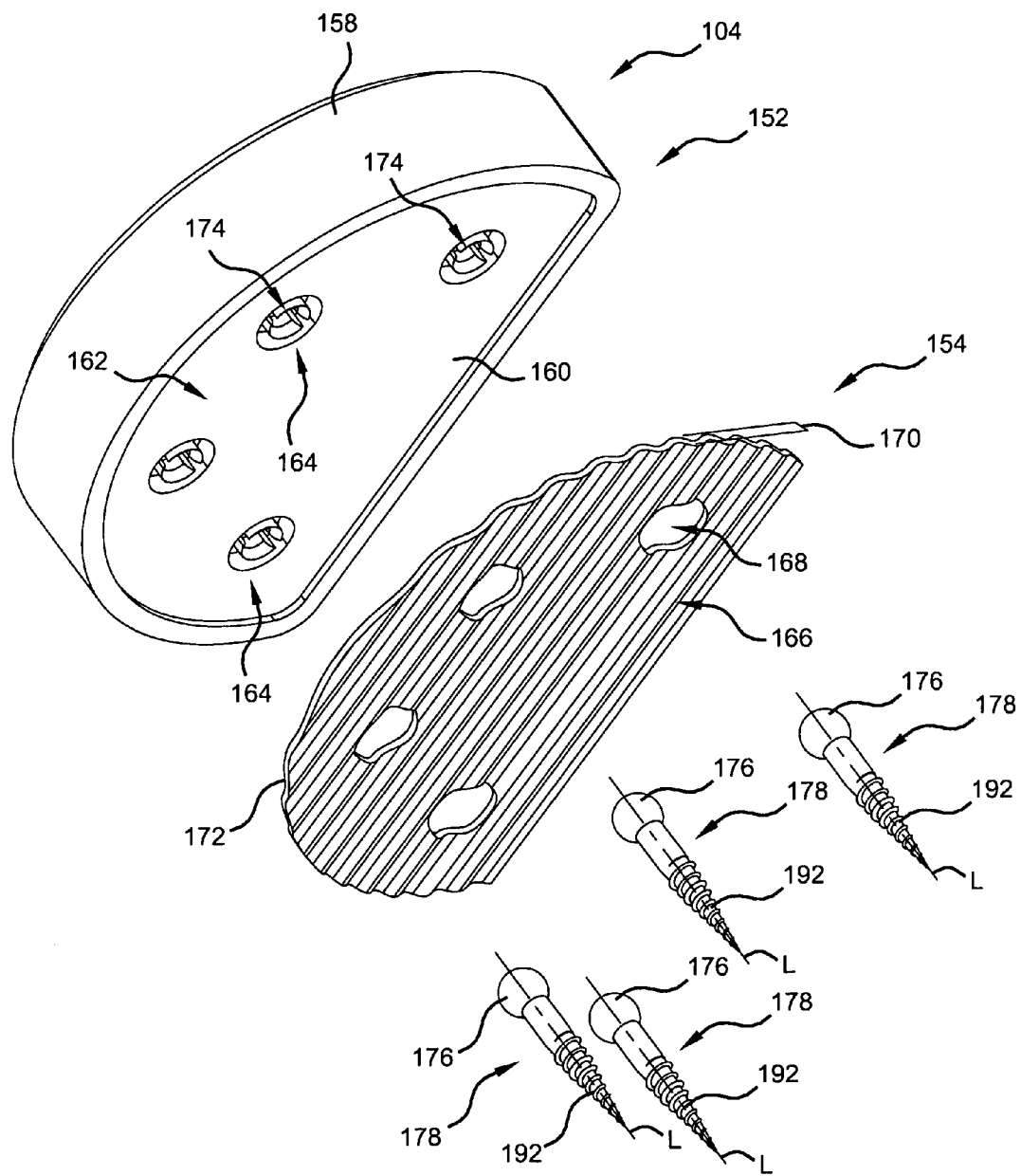
FIG. 7 is similar to FIG. 4 and shows an exploded assembly view of the tibial component including a body portion, a textured surface and bone screws that can couple to the tibial component in accordance with the present teachings.
Figure 8:
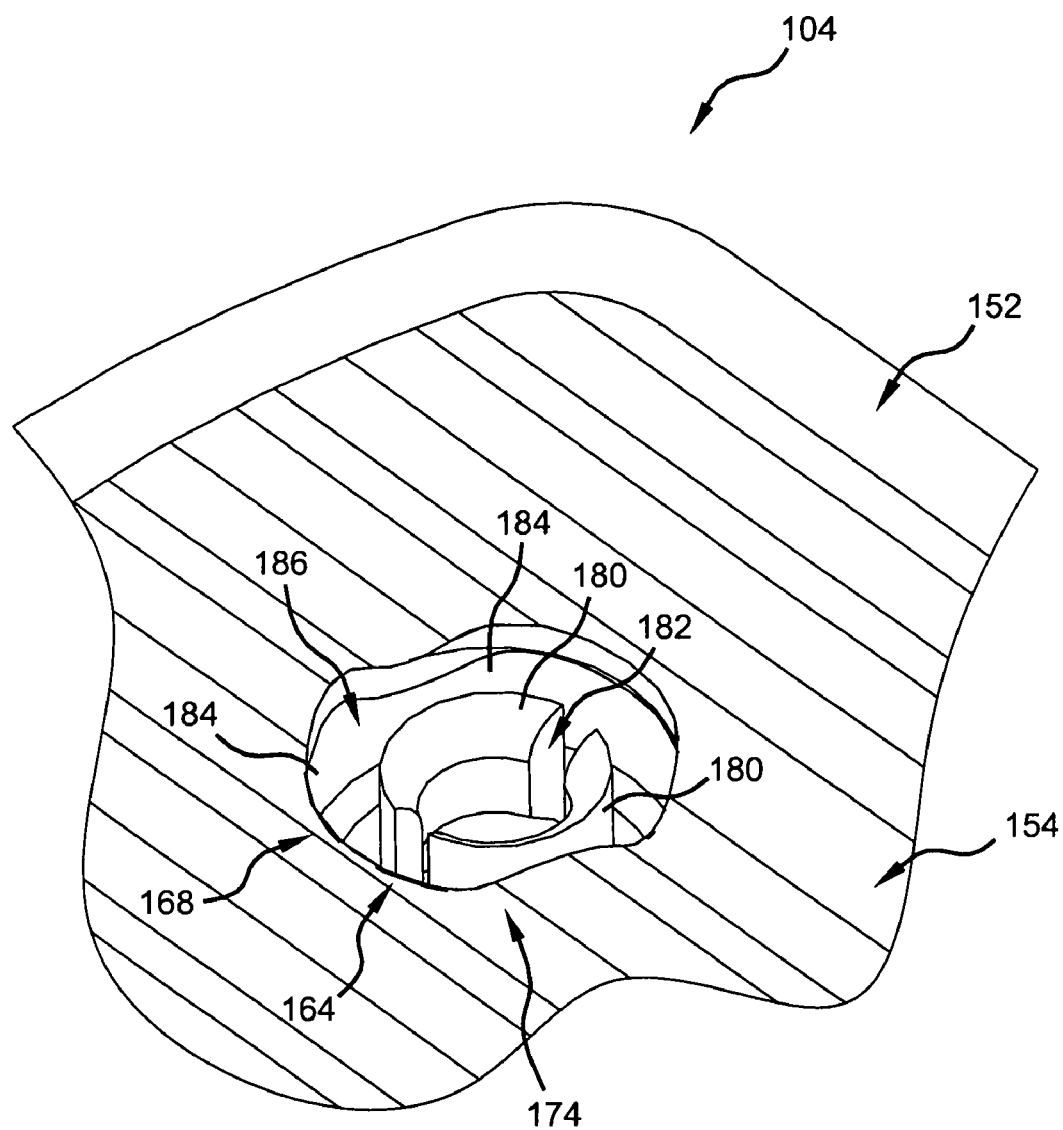
FIG. 8 is a partial perspective view of the tibial component of FIG. 7 showing a locking mechanism having compliant portions.

With reference to FIGS. 7 and 8, the tibial component 104 can generally include a first member 152 and a second member 154. The first member 152 can generally include an articulating surface 156 (FIGS. 12A and 12B), a circumferential surface 158 and a base surface 160. The base surface 160 can be generally opposite the articulating surface 156. The surfaces 156, 158, 160 can define a body portion 162. The base surface 160 can include one three, four, or more apertures 164 that extend into the body portion 162. The base surface 160 can also omit any apertures 164. The articulating surface 156 of the tibial component 104 can articulate with the articulating surface 126 (FIG. 6) of the femoral component 102, as shown in FIGS. 12A and 12B. The articulating surface 156 of the tibial component 104 can also be configured to articulate with the native bone structure 150, e.g., the femur 12 (FIGS. 1-3).

The second member 154 can include a textured portion 166 that can include one or more surfaces. In one example, the second member 154 can define one or more complementary apertures 168, which can be generally concentric with one or more of the apertures 164 formed in the body portion 162. A textured portion 166 can define the entire second member 154, i.e., generally the entire second member can be textured. The textured portion 166 can also be a portion of the second member 154 such that one or more portions of the second member 154 can have the textured portion 166 and the remaining portions of the second member 154 can have a generally planar or smooth appearance.

Figure 14A:
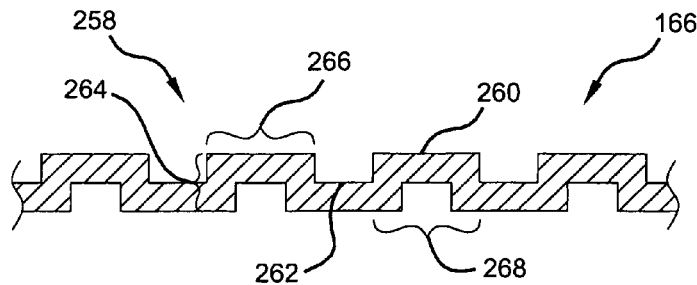
FIGS. 14A-14D are cross sectional views of textured surfaces associated with tibial components in accordance with the present teachings.
Figure 14B:
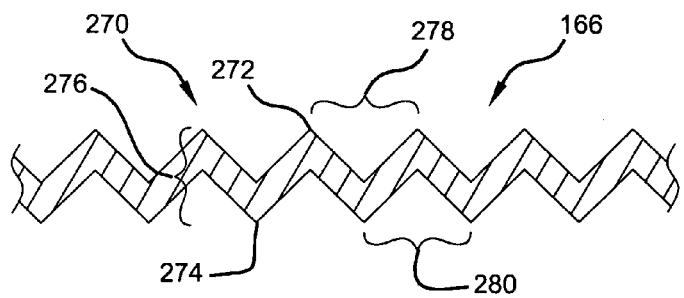
Figure 14C:
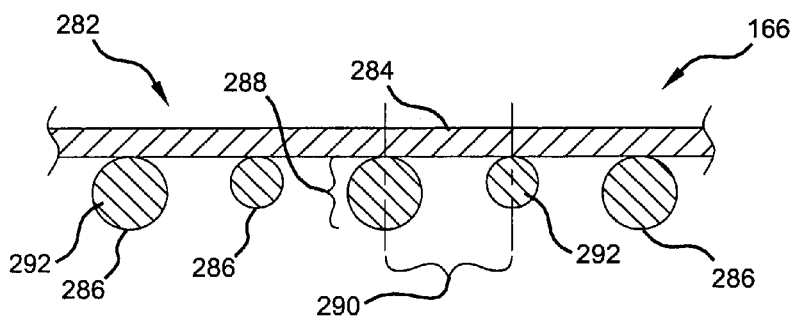
Figure 14D:
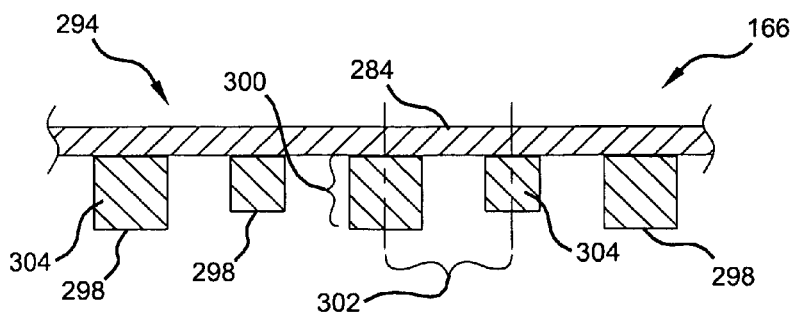
Figure 14E:
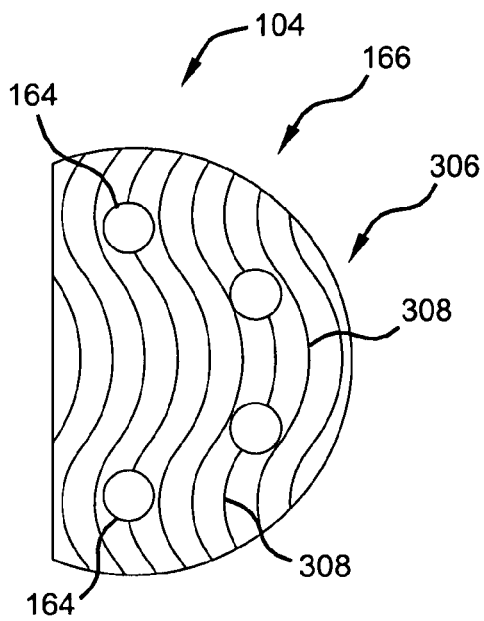
FIGS. 14E-15F are bottom views of textured surfaces associated with tibial components in accordance with the various aspects of the present teachings.

With reference to FIG. 14E, the textured portion 166 can define a wavy surface. In other aspects, the textured portion 166 can define other surface configurations and/or combinations thereof discussed in greater detail and illustrated in FIGS. 14A-15F. It will be appreciated that the textured portion 166 can have a single consistent pattern, a single varying pattern, a combination of single consistent patterns, a combination of single varying patterns and combinations thereof. For example, the textured portion 166 can have a dimension 170 (FIG. 7) defining a distance between crests and the troughs of similar structures. The dimension 170 between the crests and troughs and/or the dimension between crests (i.e., a pitch) can be constant and/or vary over the textured portion 166.

The first member 152 of the tibial component 104 can be made of a material that can be softer than the second member 154 can be. For example, the first member 152 can be generally made of ultra-high molecular weight polyethylene. The second member 154 can be generally made of titanium. The second member 154 can be partially (or completely) encapsulated by the first member 152 and thus can couple the second member 154 to the first member 152. For example, the first member 152 can encapsulate the second member 154 such that only the apertures 168 are visible (not specifically illustrated). In another example, the first member 152 can encapsulate the second member 154 such that the first member 152 can encapsulate only a periphery 172 of the second member 154 and therefore can expose all or a portion of the textured portion 166, as shown in FIG. 4 and FIG. 8.

The apertures 164 formed in the body portion 162 of the first member 152 can include a compliant locking mechanism 174 in each (or some) of the apertures 164. Each compliant locking mechanism 174 can be used to secure a ball-head 176 of a bone screw 178 to the tibial component 104. The compliant locking mechanism 174 can include two (or more) semi-annular compliant portions 180 generally opposed from one another. The compliant portions 180 can be spaced from one another and can generally define a straight channel 182 therebetween. The complaint portions 180 can also be spaced from walls 184, which can define each of the apertures 164, and thus can define an arcuate channel 186 between the complaint portions 180 and the walls 184. In another aspect, a single compliant portion 180 can be spaced from a portion of the walls 184 (not specifically shown).

Figure 9A:
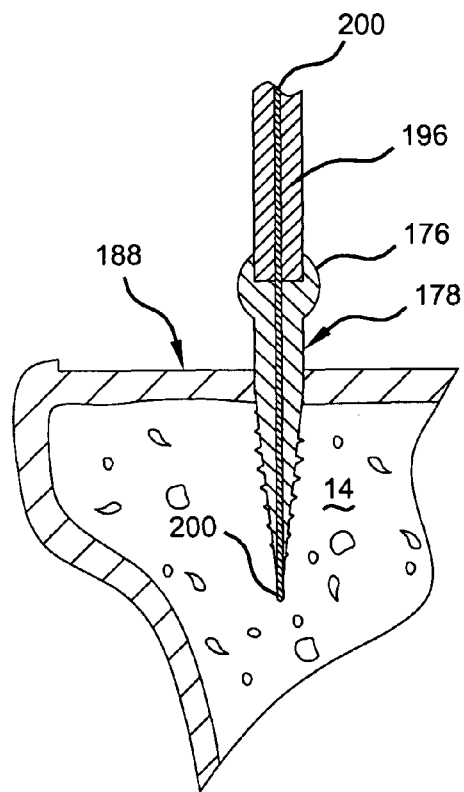
FIG. 9A is a partial cross-sectional view of a prepared tibial plateau showing a cannulated driver positioning a cannulated bone screw therein in accordance with the present teachings.

With reference to FIGS. 7 and 9A, each of the bone screws 178 (or a portion thereof) can be sized to be similar to a dental-sized bone screw and can thus be relatively smaller than typical bone screws used in previous medical procedures concerning the knee joint 10.

One or more of the bone screws 178 can be cannulated, as shown in FIGS. 5A-9B. Each of the cannulated bone screws 178 can include an elongated channel formed along (or aligned with) a longitudinal axis L (FIG. 7). The cannulation of bone screws 178 can be shown to assist the medical practitioner in inserting the bone screw 178 into a tibial plateau 188, as shown in FIG. 9A. Each of the ball-heads 176 of the bone screws 178 can be formed with a generally spherical shape (or other suitable polygonal shape). The ball-head 176 can be received by a spherical accepting cavity 190 (or other suitable and/or complementary polygonal shaped cavities) (FIG. 9B) of the tibial component 104.

Figure 9B:
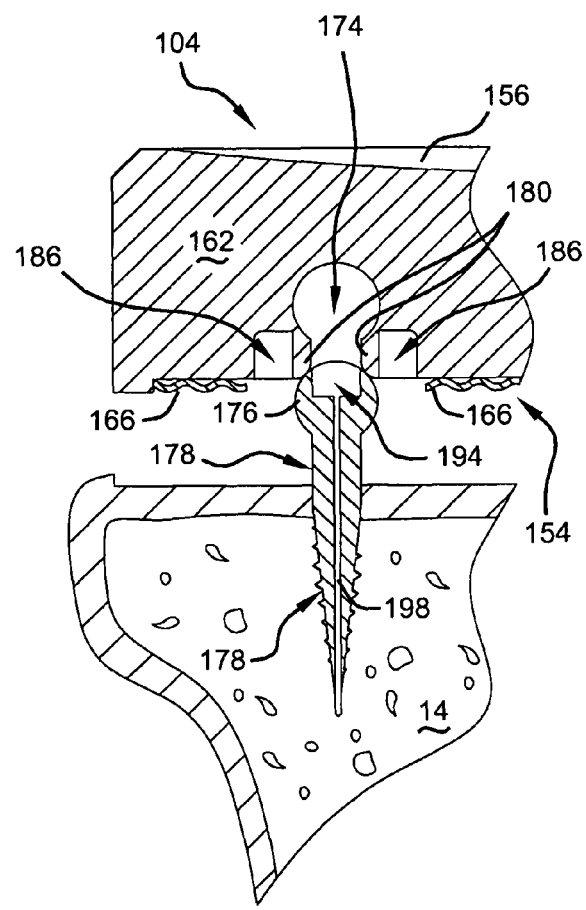
FIG. 9B is similar to FIG. 9A and shows a portion of the tibial component of FIG. 4 disposed above the cannulated bone screw.

Each of the bone screws 178 can also include mechanical threads 192 to secure the bone screw 178 to the tibial plateau 188. The ball-head 176 of each of the bone screws 178 can also include a suitable socket-head 194 (FIG. 9B) to accept a driving member 196. The suitable socket-head 194 can be formed as a Phillips head, a Torx® head, a square-drive head or other suitable shaped socket-head 194 (FIG. 9D). The longitudinal cannulation 198 (FIG. 9C) can be centered within the socket-head 194, to thus allow a guide wire 200 to be placed through the driving member 196 and through the socket-head 194. The driving member 196 can be powered manually, electrically, pneumatically, hydraulically and/or by other suitable methods or combinations thereof that produce torque.

Figure 9C:
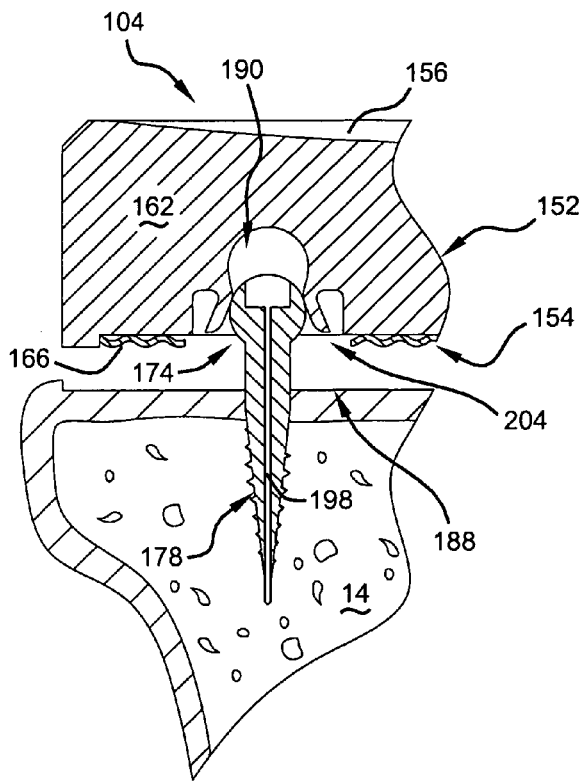
FIG. 9C is similar to FIG. 9B and shows a head of the bone screw spreading apart compliant portions of the locking mechanism as the tibial component is moved toward the tibial plates.
Figure 9D:
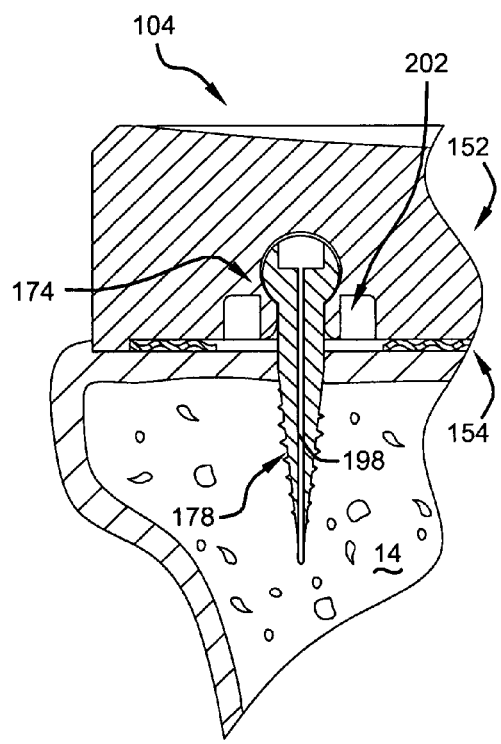
FIG. 9D is similar to FIG. 9C and shows the head of the bone screw captured by the locking mechanism thus securing the tibial component against the prepared tibial plateau.
Figure 10A:
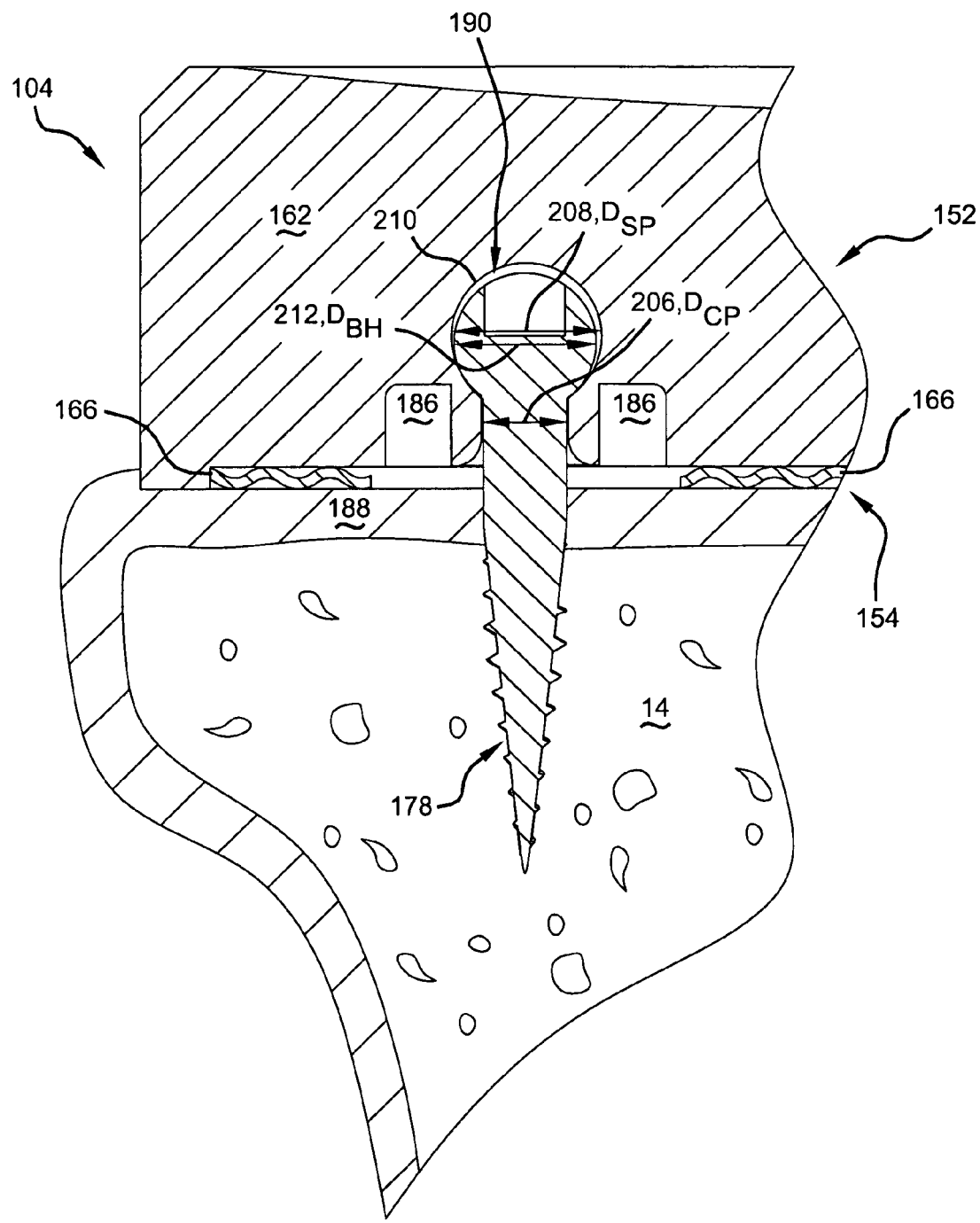
FIG. 10A is similar to FIG. 9D and shows the tibial component coupled to a bone screw without cannulation therethrough in accordance with the present teachings.

With reference to FIGS. 9C-9D, the semi-annular compliant portions 180 can move from a normal condition 202 (i.e., non-deflected) to a deflected condition 204. The ball-head 176 of the bone screw 178 can move the compliant portions 180 from the normal condition 202 to the deflected condition 204. The accepting cavity 190 can define the volume behind the semi-annular compliant portions 180. With reference to FIG. 10A, a dimension defining a distance 206 between the semi-annular compliant portions 180 (i.e., $D_{CP}$) can be less than a dimension defining a diameter 208 (i.e., $D_{SP}$) between walls 210 of the accepting cavity 190 (i.e., $D_{SP}$ about $>D_{CP}$). The accepting cavity 190 need not be spherical but can be rectangular (or other suitable polygonal shaped cavities) and as such, the distance 206 ($D_{CP}$) can be less than a dimension defining a width between walls of the rectangular portion. In one example, a dimension defining a diameter 212 of the ball-head 176 (i.e., $D_{BH}$) can be less than the diameter 208 ($D_{SP}$) (or applicable width) and can be greater than the distance 206 ($D_{CP}$) (i.e., $D_{SP}$ about $>D_{BH}$ about $>D_{CP}$).

A length of the bone screw 178 (along the axis L) can be in a range from about 8 millimeters to about 13 millimeters (about 0.3 inches to about 0.5 inches). In one aspect, a diameter of a shaft can be in a range from about 1 millimeter to about 3 millimeters (about 0.04 inches to about 0.12 inches). In a further aspect, the diameter of the shaft can be about 2 mm (about 0.08 inches). The shaft of the bone screws 178 can taper in the area of the mechanical threads 192. The thread configuration can resemble a wood screw thread, other suitable thread configurations and combinations thereof. The diameter 212 of the ball-head 176 ($D_{BH}$) can be in a range from about 3 millimeters to about 4 millimeters (about 0.12 inches to about 0.16 inches).

The tibial component 104 can be secured to the tibial plateau 188 by snapping the tibial component 104 onto the bone screws 178. With reference to FIG. 9A, one or more bone screws 178 can be secured to the tibial plateau 188 by, for example, rotating the driver member 196 to insert the bone screw 178. The guide wire 200 can be inserted through the cannulation of the driver member 196 and the bone screw 178. The driver member 196 and/or the bone screw 178 can be used without the guide wire 200 or without the cannulation 198. With reference to FIG. 9B, the ball-head 176 of the bone screw 178 can be inserted through the aperture 168 on second member 154 of the tibial component 104 and thus into the compliant locking mechanism 174.

With reference to FIG. 9C, the ball-head 176 can move the compliant locking portions 180 from the normal condition 202 (FIG. 9B) to the deflected condition 204 (FIG. 9C). With reference to FIG. 9D, the ball-head 176 can move past the compliant locking portions 180 and into the accepting cavity 190. As the ball-head 176 of the bone screw 178 passes the compliant portions 180, the compliant portions 180 can move back to the normal condition 202 from the deflected condition 204. When the compliant portions 180 move back to the normal condition 202, the ball-head 176 can be drawn in and become captured in the accepting cavity 190 (i.e., a snap fit) and thus can secure the tibial component 104 to the tibial plateau 188, as shown in FIGS. 9D and 10A.

Figure 10B:
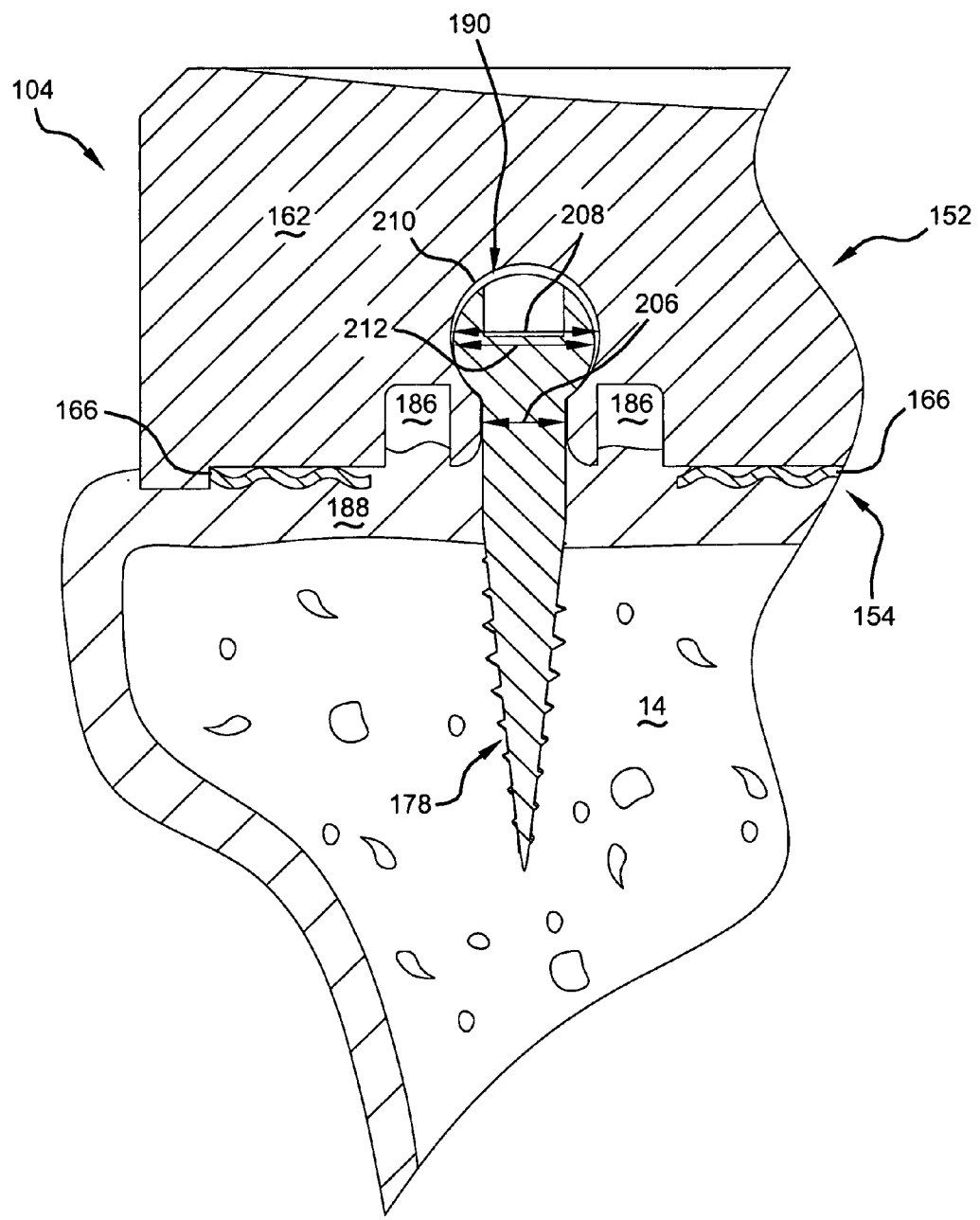
FIG. 10B is similar to FIG. 10A and shows bone in-growth around the tibial component.

With reference to FIG. 10A, the tibial component 104 is illustrated in contact with the tibial plateau 188 shortly after implantation of the tibial component 104. With reference to FIG. 10B, the tibial component 104 is shown in contact the tibial plateau 188 after a period in which the bone in-growth can occur. With reference to FIGS. 9D, 10A and 10B, the tibial component 104 can be held against the tibial plateau such that the tibial component 104 exerts a force on the tibial plateau 188 because the snap-fit connection of the ball heads 176 of the bone screws 178 to the compliant locking mechanism 174 can generate the force to pull the tibial component 104 toward the tibial plateau 188. As a reaction to that force, it can be shown that bone in-growth can occur around the first member 152 and/or the second member 154 of the tibial component 104, as shown in FIG. 10B. With reference to FIG. 10B, the bone in-growth can occur around the textured portion 166, which can be shown to result in new bone filling into the textured portion 166. It can be shown that the bone in-growth into or around the textured portion 166 can provide a more secure installation relative to a tibial component without the textured portion.

Figure 11A:
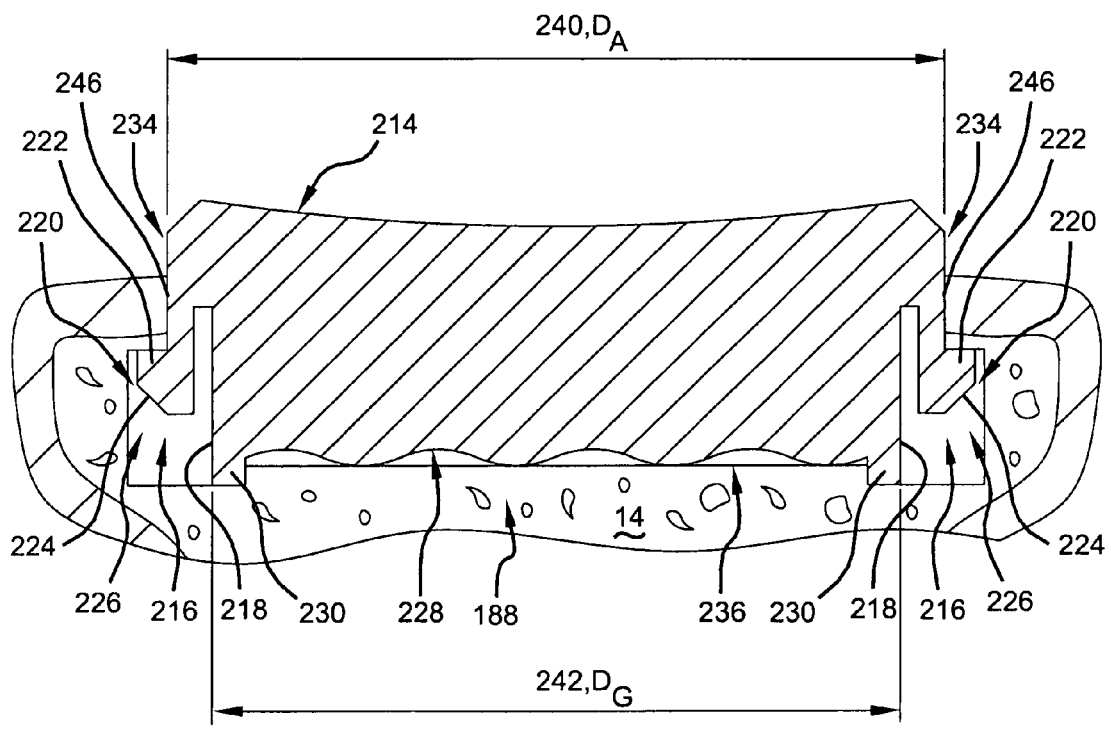
FIG. 11A is a partial cross-sectional view of a tibial component secured to a tibial plateau in accordance with another aspect of the present teachings.
Figure 11B:
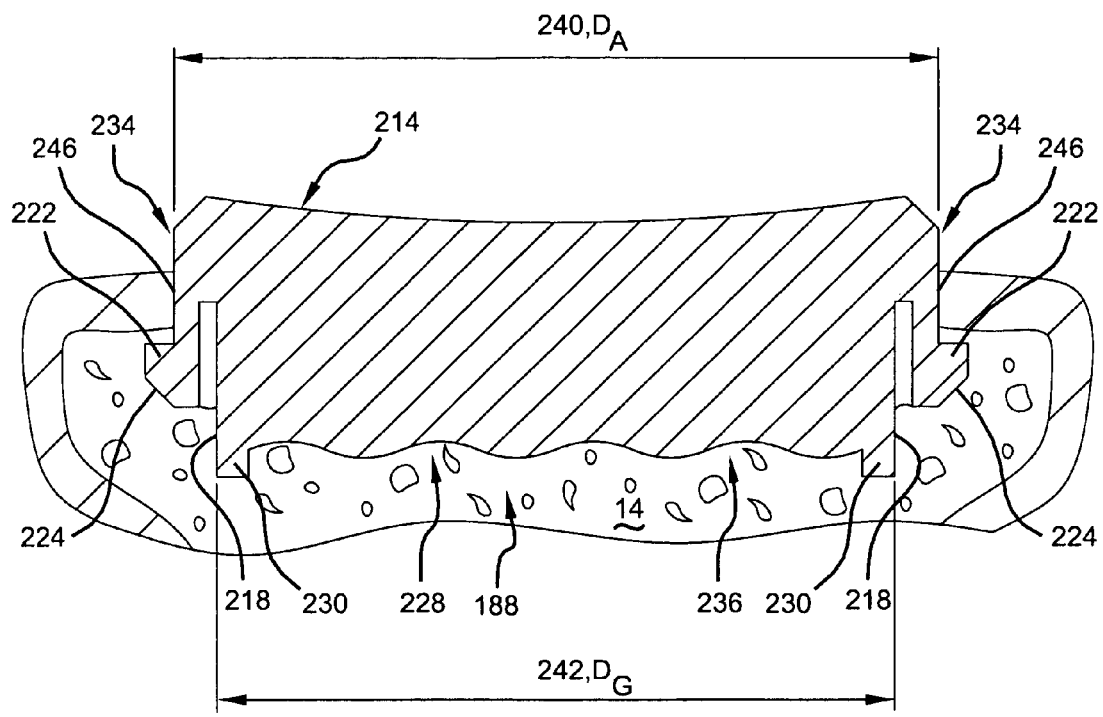
FIG. 11B is similar to FIG. 11A shows bone in-growth around the tibial component.

With reference to FIGS. 11A and 11B, an alternative tibial component 214 can be formed with a locking rim 216 generally around a periphery 218 of the tibial component 214. A complimentary locking rim structure 220 can be formed in the tibial plateau 188 and can receive the locking rim 216 formed on the tibial component 214. The tibial component 214 can include one or more flanges 222. For example, the tibial component 214 includes a pair of the flanges 222 that are generally opposite each other on the first member 222. Each flange 222 can include a protrusion 224 that can engage a groove 226 that can be formed in the tibial plateau 188.

The tibial component 214 can also include a textured portion 228 that can be similar to the textured portion 166, as shown in FIGS. 7 and 14. In one example, the textured portion 228 can be recessed into the tibial component 214 such that walls 230 can bound the textured portion 228. The textured portion can also form the bottom (or a portion thereof) of the tibial component 214 and, as such, may not recessed.

Figure 15A:
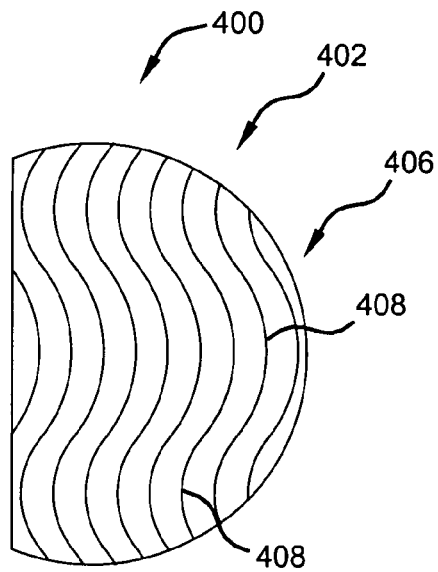

In one example, the tibial plateau 188 can be configured to accept the tibial component 104 (FIG. 4), the tibial component 214 (FIG. 11A) or the tibial component 400 (FIG. 15A). Regardless of what is used, the menisci and/or other native materials of the knee joint 10 may need to be removed or resected from the tibia 14 unless already absent due to myriad medical concerns. Once the superior articular surfaces 232 (FIG. 3) of the tibia 14 are exposed, the tibia 14 can be prepared to accept the tibial component 104, 214, 400. It will be appreciated that only the medial superior articular surface or the lateral superior articular surface need to be prepared to accept the tibial component 104, 214, 400 of the unicompartmental knee implantation system 100 in accordance with the various aspects of the present teachings.

With reference to FIGS. 11A and 11B, the tibia 14 can be prepared to accept the tibial component 214. An aperture 234 can be formed in the tibia 14 that can have two of the grooves 226 and a raised portion 236. The aperture 234 can be open on one end to permit sliding of the tibial component 214 into the aperture 234 in a direction that can be generally perpendicular to a longitudinal axis 238 (FIG. 3) of the tibia 14. The aperture 234 can also be configured to accept the tibial component 214 in a direction that can be generally coaxial with the longitudinal axis 238 of the tibia 14.

The aperture 234 can define a dimension 240 (i.e., $D_A$) spanning the opening of the aperture 234. The grooves 226 can further expand a portion of the aperture 234 such that a dimension 242 (i.e., $D_G$) between the sides 244 of the grooves 226 can be greater than the dimension 240 ($D_A$) (i.e., $D_G$ about $>D_A$). Because the grooves 226 can further expand a portion of the aperture 234, a lip 246 can be defined by the aperture 234 and, as such, the dimension 240 ($D_A$) can be defined by a distance (i.e., the size of the opening) between the lips 246. The raised portion 236 can be sized to fit into the recessed portion of the tibial component 214 and thus can contact the wavy portion 228.

The flanges 222 of the locking rim 216 can be positioned in the grooves 226 of the aperture 234 to secure the tibial component 214 to the tibia 14. The flanges 222 can be deflected when positioned in the aperture 234 (i.e., an implanted position), such that a spring force can be applied to the lips 246 of the aperture 234 and/or other portions of the tibia 14. It may be shown that the spring force further secures the tibial component 214 to the tibia 14. As such, the position of the tibial component 214 causes the textured portion 228 to exert a force on the raised portion 236 and/or other portions of the tibial plateau. It may be shown that the force exerted on the raised portion 236 and/or other portions of the tibial plateau may promote bone in-growth into the textured portion 228.

With reference to FIGS. 15A-15F, the textured portions of the tibial components 400 can be similar to the tibial component 104 but can omit the apertures 164 and can thus omit the compliant locking mechanisms 174. The textured portions 402 will be discussed in further detail. The tibial component 400 can be secured to the tibial plateau 188 with bone cement and/or other suitable bonding materials.

With reference to FIGS. 3, 12A and 12B, the femoral component 102 and/or the tibial component 104, 214, 400 can attach to either the medial (FIG. 12A) or the lateral (FIG. 12B) condyles of the femur 12 and the tibia 14, respectfully. In one example, the inferior end of the femur 12 can be prepared by resecting a portion of either the medial or lateral condyles. The portion of the condyle can be further prepared (e.g., reamed and/or chiseled) to receive the femoral component 102.

With reference to FIGS. 3 and 4, the web keel 110 of the femoral component 102 can be generally aligned with an anterior-posterior plane 248 of the femur 12 (FIG. 3). The cross-web keel 112 can be generally perpendicular to the web keel 110 and thus be generally aligned with a medial-lateral plane 250 of the femur 12. The femoral component 102 can be inserted in the resected portions of the respective condyles. The peg 106, the web keel 110, the cross-web keel 112 or portions thereof can be received by an intramedullary canal 252.

With reference to FIG. 3, it will be appreciated that the anterior-posterior plane 248 and the medial-lateral plane 250 are not exactly and specifically located on the body but can provide general guidance as to orientation and location. As such, alignment of the web keel 110 (FIG. 4) to the anterior-posterior plane 248 and cross-web keel 112 (FIG. 4) to the medial-lateral plane 250 can provide a general orientation of the femoral component 102 relative to the femur 12.

With reference to FIG. 3, the incision 134 can be a medial parapatellar incision and can be made proximate to the knee joint 10. The incision 134 can be of a minimally invasive type, thus the incision 134 can have an overall length of approximately 3 inches to approximately 5 inches (approximately 76 millimeters to approximately 127 millimeters). The incision (or multiple incisions) can be made at various locations around the knee joint 10 and can aid in insertion of the femoral component 102 and/or the tibial component 104. While a minimally invasive incision 136 can be used, the femoral component 102 and/or the tibial component 104 can be compatible with other incisions and/or other suitable medical equipment. For example, the tibial component 104 and/or the femoral component 102 can be passed through a cannula and into the incision 134. The configuration of the peg 106, the web keel 110 and/or the cross-web keel 112, as above-described, may be shown to reduce the propensity of hanging up or catching on the walls of the cannula.

Figure 13:
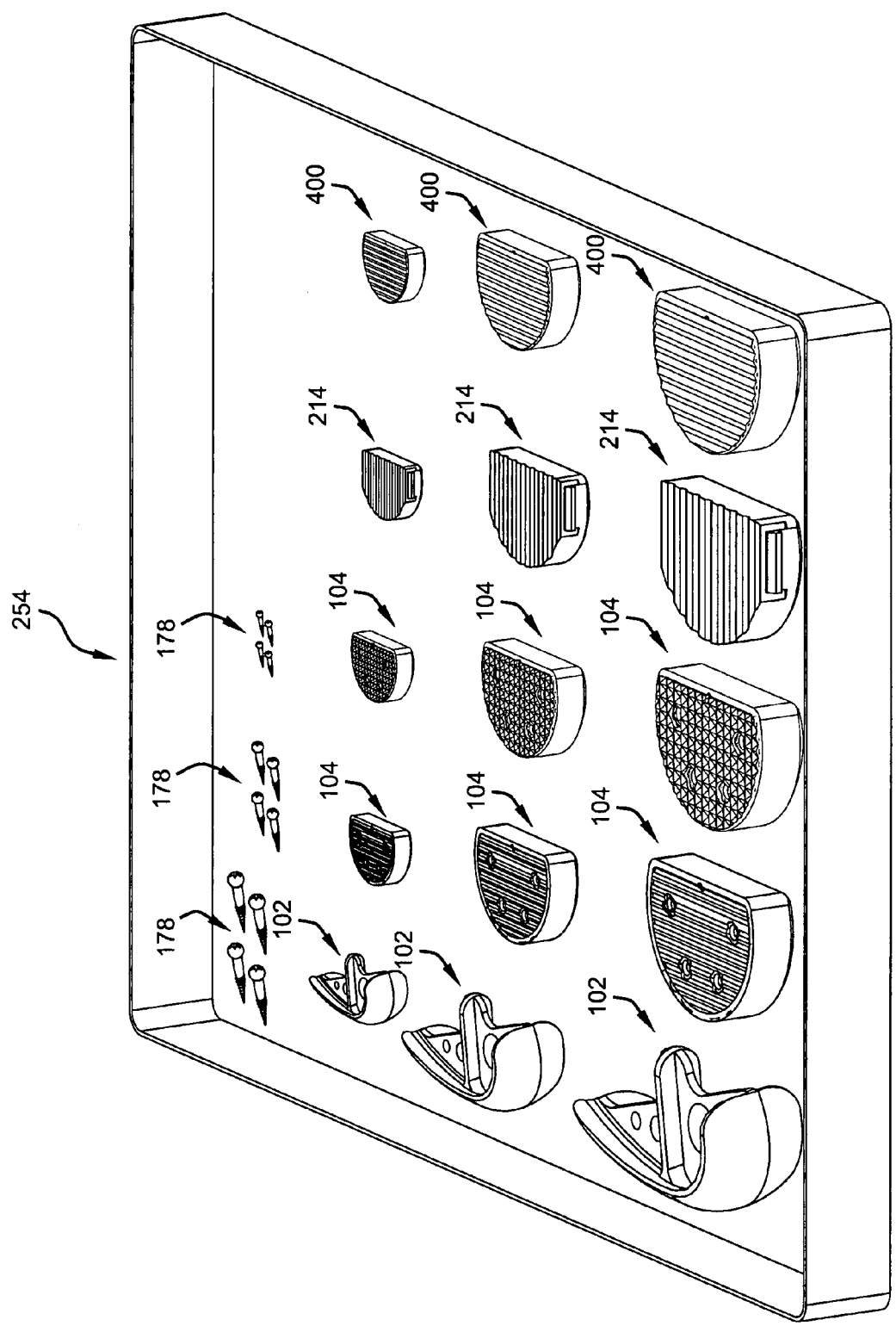
FIG. 13 is a perspective view of a kit including varying sizes and/or configurations of tibial components, femoral component and bone screws constructed in accordance with the various aspects of the present teachings.

With reference to FIG. 13, a kit 254 is shown constructed in accordance with the present teachings. The kit 254 can include a plurality of femoral components 102 having varying peg lengths, diameters, concavities and/or other suitable femoral component configurations. The kit 254 can also include a plurality of the tibial components 104, 214, 400. The tibial components 104, 214, 400 can also include varying sizes, configurations, degree of encapsulation, textured surface configurations, and number of locking mechanisms formed on the tibial component 104, 214, 400, as applicable. The kit 254 can also include a plurality of bone screws 178 having varying lengths, widths, bone screw thread configurations and cannulated and non-cannulated configurations (not specifically shown).

In one example and with reference to FIGS. 14A-15F, alternative configurations 256 of the textured portion 166, 402 are illustrated in accordance with the various aspects of the present teachings. With reference to FIG. 14A, the textured portion 166 can include a square-wave pattern 258 that can have a top surface 260 (i.e., similar to a crest) and a respective bottom surface 262 (i.e., similar to a trough). The square wave pattern 258 can include a height 264 between the top surface 258 and the bottom surface 260. The top surface 260 can include a width 266 and the bottom surface 260 can include a width 268. The height 264, the width 266 and/or the width 268 can be uniform, varied or combinations thereof throughout the textured portion 166.

With reference to FIG. 14B, the textured portion 166 can include a saw tooth pattern 270 that can have a top peak 272 (i.e., similar to a crest) and a respective bottom peak 274 (i.e., similar to a trough). The saw tooth wave pattern 270 can include a height 276 between the top peak 272 and the bottom peak 274. Two adjacent top peaks can include a distance 278 therebetween and two adjacent bottom peaks 274 can include a distance 280 therebetween. The height 276, the distance 278, and/or the distance 280 can be uniform, varied, or combinations thereof throughout the textured portion 166.

With reference to FIG. 14C, the textured portion 166 can include a repeating cylindrical protrusion pattern 282 that can have a top surface 284 and a plurality of bottom surfaces 286. The pattern 282 can include a height 288 between the top surface 284 and each bottom surface 286. A pitch 290 can be defined between two of the cylindrical portions 292 (i.e., a distance therebetween). The height 288, the pitch 290, the configuration of the cylindrical protrusions and combinations thereof can be uniform, varied, or combinations thereof throughout the textured portion 166.

With reference to FIG. 14D, the textured portion 166 can include a repeating rectangular protrusion pattern 294 that can have a top surface 296 and a respective bottom surface 298. The repeating rectangular pattern 294 can include a height 300 between the top surface 296 and the bottom surface 298. A pitch 302 can be defined between two rectangular portions 304 in the repeating rectangular pattern 294. The height 300, the pitch 302, the configuration of the repeating rectangular protrusions and/or combinations thereof can be uniform, varied, or combinations thereof throughout the textured portion 166.

With reference to FIGS. 14E and 15A, the textured portion 166, 402 can include a wavy pattern 306, 406. The wavy pattern 306, 406 can include a plurality of wave shaped grooves 308, 408. The wave shaped grooves 308, 408 can be parallel to one another, intersect one another and/or be arranged in a random pattern. The apertures 164 can be formed through the textured portion 166 and can be omitted from the textured portion 402.

Figure 14F:
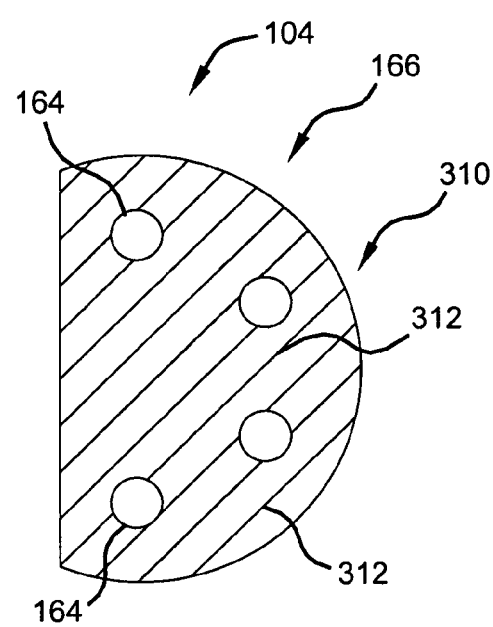
Figure 15B:
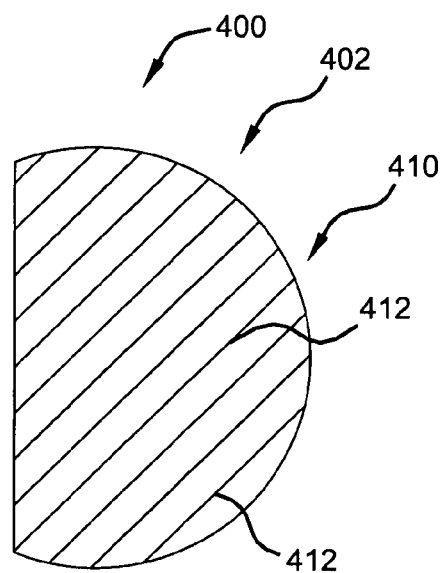

With reference to FIGS. 14F and 15B, the textured portion 166, 402 can include a diagonal line pattern 310, 410. The diagonal line pattern 310, 410 can include a plurality of diagonal grooves 312, 412. The diagonal grooves 312, 412 can be formed parallel to one another, intersect one another, and/or can be formed in a random pattern.

Figure 14G:
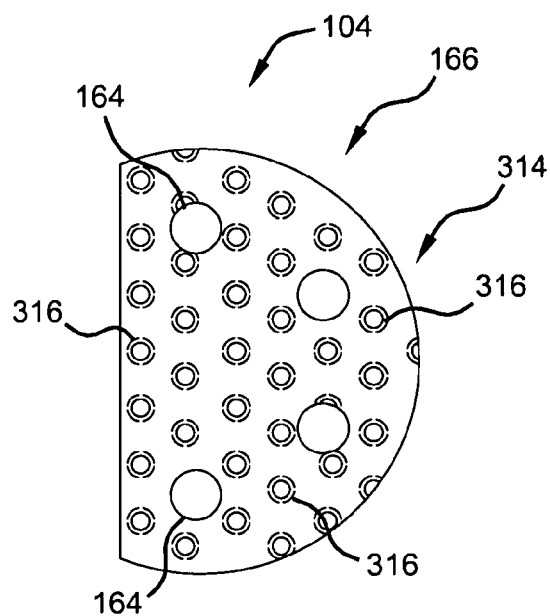
Figure 15C:
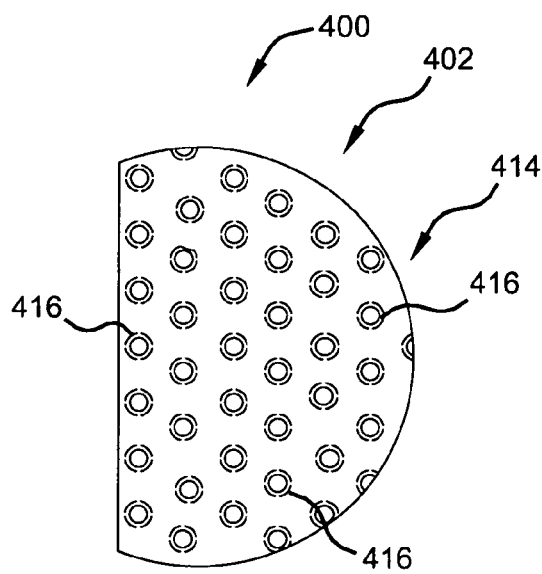

With reference to FIGS. 14G and 15C, the textured portion 166, 402 can include a dimple pattern 314, 414. The dimple pattern 314, 414 can include a plurality of dimples 316, 416. The dimples 316, 416 can have varying sizes, varying depths and/or varying shapes. The dimples 316, 416 can be arranged in rows and/or columns or also can be arranged in a random pattern.

Figure 14H:
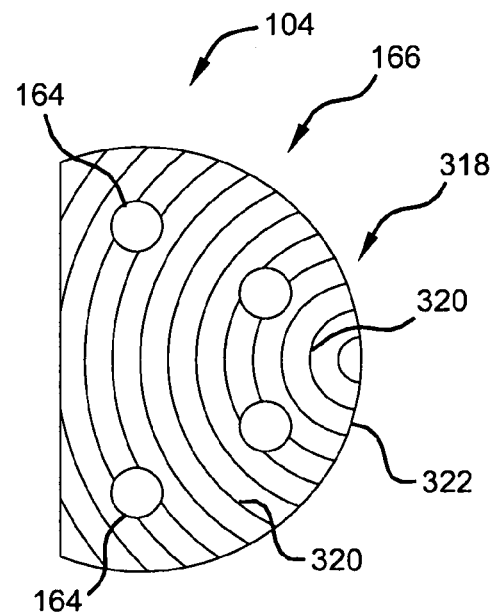
Figure 15D:
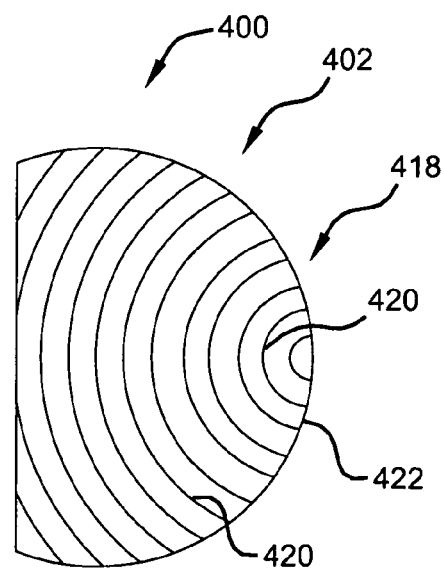

With reference to FIGS. 14H and 15D, the textured portion 166, 402 can include a radiating line pattern 318, 418. The radiating line pattern 318, 418 can include a plurality of radiating grooves 320, 420 from a side 322, 422 of the textured portion 166, 402. The radiating grooves 320, 420 can be formed in semi-annular shapes. The width and/or curvature of the radiating grooves 320, 420 can be uniform and/or random throughout portions of the textured portion 166, 402.

Figure 15E:
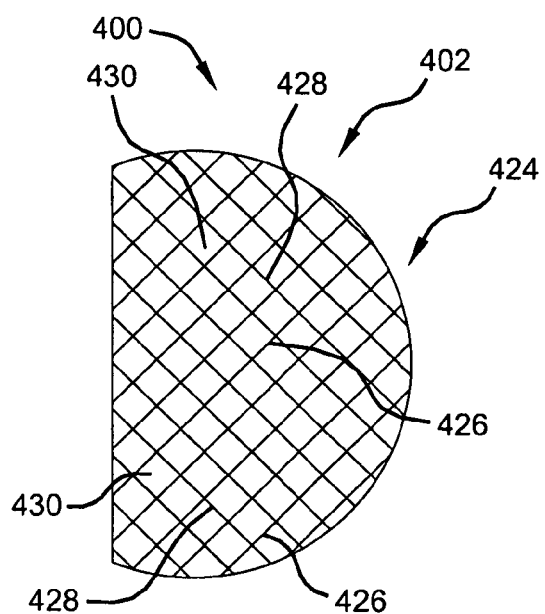

With reference to FIGS. 14I and 15E, the textured portion 166, 402 can include a mesh pattern 324, 424. The mesh pattern 324, 424 can include a first set of line members 326, 426 generally perpendicular to a second set of line members 328, 428 that can form a plurality of wells 330, 430 therebetween. It may be shown that the plurality of wells 330, 430 promote bone ingrowth and, therefore, may be shown to secure the tibial components 104, 400 to the tibial plateau 188.

Figure 15F:
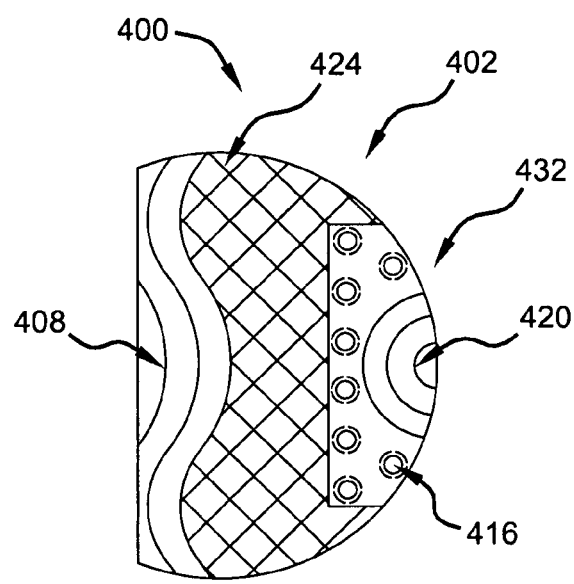

With reference to FIGS. 14J and 15F, the textured portion 166, 402 can include a plurality of patterns 332, 442. The plurality of patterns 332, 442 can include one or more of the above disclosed patterns 306, 406, 310, 410, 314, 414, 318, 418, 324, 424. The amount of each of the above patterns, the configuration of each pattern and the position of each pattern relative to another pattern may be uniform, varied or a combination thereof. The configuration of each pattern or the configuration of certain patterns relative to other patterns may be based on the native bone structure.

While specific aspects of the present teachings have been described in the specification and illustrated in the drawings, it will be understood by those skilled in the art that various changes may be made and equivalence may be substituted for elements thereof without parting from the scope of the present teachings, as defined in the claims. Furthermore, the mixing and matching of features, elements and/or functions between various aspects is expressly contemplated herein so that one skilled in the art would appreciate from the present teachings that features, elements and/or functions of one aspect may be incorporated into another aspect of the present teachings as appropriate, unless described otherwise above. Moreover, many modifications can be made to adapt a particular situation or material to the present teachings without departing from the scope thereof. Therefore, it is intended that the various aspects of the present teachings not be limited to the particular examples illustrated by the drawings and described in the specification as the best mode presently contemplated for carrying out the present teachings but that the scope of the present teachings will include any aspects following within the foregoing description and defined in the appended claims.

What is claimed is:

1. A knee implantation system for replacing a portion of a knee joint, the knee implantation system comprising:
    an unicondyler tibial implant configured to replace a portion of a tibia, said tibial implant including a first member and a second member;
    said first member having a body portion that includes an articulating surface for replacing only a single superior articulating surface of the tibia;
    said second member having a textured surface, said second member is removably connected to said body portion and said textured surface is disposed about opposite said articulating surface;
    at least one locking mechanism formed in and integrally coupled to said body portion of said first member such that said at least one locking mechanism and said body portion are monolithic, and at least one aperture formed in said textured surface of said second member, at least one bone screw having a head and a shaft, said head is wider than said shaft,
    wherein said locking mechanism defines an accepting cavity in said body portion disposed adjacent at least a first compliant portion,
    wherein said first compliant portion is operable to resiliently deflect between a first position and a second position, the first compliant portion resiliently deflecting from said first position toward said second position due to passage of said head of said bone screw past the first compliant portion to move said head through said aperture in said textured surface and into said accepting cavity in said body portion, said first compliant portion also resiliently deflecting from said second position to said first position to retain said head within said accepting cavity.

2. The knee implantation system of claim 1 wherein a width or a diameter of said head of said bone screw is in a range from about two millimeters to about four millimeters, a diameter of said shaft is about two millimeters and a length of said bone screw is in range of about eight millimeters to about thirteen millimeters.

3. The knee implantation system of claim 1 wherein said first member at least partially encapsulates said second member.

4. The knee implantation system of claim 1 wherein said textured surfaces has a cross-sectional configuration selected from a group consisting of a wave surface, a square wave pattern, a saw tooth pattern, a cylindrical protrusion pattern, a rectangular protrusion pattern, a wavy pattern, a diagonal line pattern, a dimple pattern, radiating line pattern, a mesh pattern, a random pattern and combinations thereof.

5. The knee implantation system of claim 1 further comprising a femoral implant having an articulating surface and a base surface disposed generally opposite said articulating surface of said femoral implant, said articulating surface of said femoral implant operable to articulate about said articulating surface of said tibial implant and said femoral implant includes a peg and a wall extending from said base surface, wherein said wall defines a web keel and a cross-web keel extending from said web keel and wherein at least one of said web keel and said cross-web keel includes a web portion defining at least one aperture adapted to promote bone ingrowth.

6. The knee implantation system of claim 1 further comprising a plurality of unicondyler tibial implants having varying sizes of at least one of body portions, textured surfaces and articulating surfaces of said tibial implants.

7. The knee implantation system of claim 1, wherein said locking mechanism defines an accepting cavity in said body portion disposed adjacent a first compliant portion and a second compliant portion, and wherein said locking mechanism includes an aperture formed in said body portion in which said first and second compliant portions are disposed, wherein said aperture establishes an arcuate channel between a wall that defines said aperture and said first and second compliant portions to permit said first and second compliant portions to deflect and accept said head of said bone screw.

8. A knee implantation system for replacing a portion of a knee joint, the knee implantation system comprising:
    a tibial implant having a body portion defining an articulating surface;
    a plurality of femoral implants, each having an articulating surface and an arcuate base surface disposed generally opposite said articulating surface of said femoral implant, each of said articulating surfaces of said femoral implant operable to articulate about said articulating surface of said tibial implant, each of said articulating surfaces of said femoral implant having an anterior side and a posterior side;
    each of said plurality of femoral implants including a peg and a wall extending from said arcuate base surface, said pegs of said plurality of femoral implants having varying heights,
    wherein for each of said plurality of femoral implants, said wall terminates at a top edge that defines an imaginary plane,
    wherein for each of said plurality of femoral implants, said wall includes a first portion extending between said anterior side and said peg and a second portion extending between said posterior side and said peg, and wherein said first portion and said second portion of said wall each terminate at said imaginary plane, wherein for each of said plurality of femoral implants, said imaginary plane intersects said peg and said articulating surface adjacent the anterior side, and wherein said imaginary plane is spaced apart at a distance from said articulating surface adjacent said posterior side to be in a non-intersecting relationship with said articulating surface adjacent the posterior side, and wherein for each of said plurality of femoral implants, a value of a height of said wall adjacent to said peg is greater than or equal to a value of a height of said peg minus a value of a width or a diameter of said peg.

9. The knee implantation system of claim 8 wherein for each of said plurality of femoral implants, said wall defines a web keel and a cross-web keel extending from said web keel, wherein in at least one of said web keel and said cross-web keel includes a web portion defining at least one aperture adapted to promote bone in-growth.

10. A knee implantation system for replacing a portion of a knee joint, the knee implantation system comprising:
 a tibial implant having a body portion defining an articulating surface;
 a femoral implant having an articulating surface and an arcuate base surface disposed generally opposite said articulating surface of said femoral implant, said articulating surface of said femoral implant operable to articulate about said articulating surface of said tibial implant, said articulating surface of said femoral implant having an anterior side and a posterior side;
 a peg and a wall extending from said arcuate base surface, wherein said wall terminates at a top edge that defines an imaginary plane,
 wherein said imaginary plane intersects said peg and is spaced apart at a distance from said articulating surface adjacent said posterior side to be in a non-intersecting relationship with said articulating surface adjacent the posterior side, and
 wherein a value of a height of said wall adjacent to said peg is greater than or equal to a value of a height of said peg minus a value of a width or diameter of said peg.

11. A knee implantation system for replacing a portion of a knee joint, the knee implantation system comprising:
 a tibial implant having a first member and a second member, said first member having a body portion that includes an articulating surface, said second member includes a textured surface, wherein said textured surface is disposed generally opposite said articulating surface and said textured surface has a cross-sectional configuration selected from a group consisting of a wave surface, a square wave pattern, a saw tooth pattern, a cylindrical protrusion pattern, a rectangular protrusion pattern, a wavy pattern, a diagonal line pattern, a dimple pattern, radiating line pattern, a mesh pattern, a random pattern and combinations thereof;
 a femoral implant having an articulating surface and a base surface disposed generally opposite said articulating surface of said femoral implant, said articulating surface of said femoral implant operable to articulate about said articulating surface of said tibial implant and said femoral implant includes a peg and a wall extending from said base surface, wherein said wall defines a web keel and a cross-web keel extending from said web keel and wherein at least one of said web keel and said cross-web keel includes a web portion defining at least one aperture adapted to promote bone in-growth;
 at least one locking mechanism defined by and integrally coupled to said body portion such that said at least one locking mechanism and said body portion are monolithic, said locking mechanism defines an accepting cavity disposed behind a first complaint portion and a second compliant portion;
 at least one bone screw having a head and a shaft,
 wherein said first compliant portion and said second compliant portion are opposed to one another and are operable to resiliently deflect toward each other and away from each other, said first and second compliant portions deflecting away from each other due to passage of said head of said bone screw past said first and second compliant portions to move said head through an aperture in said textured surface and into said accepting cavity, said first and second compliant portions also resiliently deflecting toward each other to retain said head within said accepting cavity.

12. The knee implantation system of claim 11 wherein said accepting cavity has a width or a diameter generally greater than a distance between said first complaint portion and said second compliant portion.

13. The knee implantation system of claim 12 comprising a plurality of femoral implants and a plurality of tibial implants, said femoral implants having a plurality of pegs and a plurality of walls, at least one of said pegs or said walls varying in height among the plurality of femoral implants, said tibial implants having a plurality of body portions, textured surfaces and articulating surfaces, at least one of said body portions, said textured surfaces and said articulating surfaces varying in size among the plurality of tibial implants.

14. The knee implantation system of claim 11 wherein said head of said bone screw has a complementary shape to said accepting cavity and wherein a width or a diameter of said head of said bone screw is in a range from about two millimeters to about four millimeters, a diameter of said shaft is about two millimeters and a length of said bone screw is in range of about eight millimeters to about thirteen millimeters.

15. The knee implantation system of claim 11 wherein said first member at least partially encapsulates said second member of said tibial implant.

16. The knee implantation system of claim 11, wherein said locking mechanism includes an aperture formed in said body portion in which said first and second compliant portions are disposed, wherein said aperture establishes an arcuate channel between a wall that defines said aperture and said first and second compliant portions to permit said first and second compliant portions to deflect and accept said head of said bone screw.

17. A knee implantation system for replacing a portion of a knee joint, the knee implantation system comprising:
 a tibial implant having a monolithic body portion that includes an articulating surface and a textured surface that is disposed generally opposite said articulating surface, wherein said textured surface has a cross-sectional configuration that includes at least one of a wave surface, a square wave pattern, a saw tooth pattern, a cylindrical protrusion pattern, a rectangular protrusion pattern, a wavy pattern, a diagonal line pattern, a dimple pattern, radiating line pattern, a mesh pattern, a random pattern and one or more combinations thereof;
 a first flange that extends from a first area of said body portion of said tibial implant, the first area being disposed in spaced relationship from the textured surface;
 a first protrusion that extends from said first flange away from said body portion in a direction that is generally parallel to said textured surface;

a second flange that extends from a second area of said body portion of said tibial implant opposite said first flange, the second area being disposed in spaced relationship from the textured surface;

a second protrusion that extends from said second flange away from said body portion in a direction that is generally parallel to said textured surface and opposite said first protrusion, wherein said first and second protrusions are operable to engage an internal portion of the tibia, wherein a portion of each of said first flange and said second flange is flexible and operable to generate a force when said first and second flanges are deflected inward toward said body portion to secure the tibial implant to the tibia and hold said textured surface to said internal portion of the tibia.

18. The knee implantation system of claim 17 further comprising a femoral implant having an articulating surface and a base surface disposed generally opposite said articulating surface of said femoral implant, said articulating surface of said femoral implant operable to articulate about said articulating surface of said tibial implant and said femoral implant includes a peg and a wall extending from said base surface, wherein said wall defines a web keel and a cross-web keel extending from said web keel and wherein at least one of said web keel and said cross-web keel includes a web portion defining at least one aperture adapted to promote bone in-growth.

19. The knee implantation system of claim 17, wherein a first space is defined between said first flange and said body portion, wherein a second space is defined between said second flange and said body portion, and wherein the first and second spaces are reduced in size when said first and second flanges are deflected inward toward said body portion.

20. A knee implantation system for replacing a portion of a knee joint, the knee implantation system comprising:

an unicondyler tibial implant configured to replace a portion of a tibia, said tibial implant including a first member and a second member;

said first member having a body portion that includes an articulating surface for replacing only a single superior articulating surface of the tibia;

said second member having a textured surface, said second member is removably connected to said body portion and said textured surface is disposed about opposite said articulating surface;

at least one locking mechanism formed in and integrally coupled to said body portion of said first member such that said at least one locking mechanism and said body portion are monolithic, and at least one aperture formed in said textured surface of said second member, at least one bone screw having a head and a shaft, said head is wider than said shaft, wherein said locking mechanism includes a first compliant portion and a second complaint portion each having a semi-annular shape and said first compliant portion is disposed opposite said second compliant portion to establish a pair of channels between said first compliant portion and said second compliant portion, wherein said locking mechanism defines an accepting cavity in said body portion disposed adjacent said first compliant portion and said second compliant portion, wherein said first compliant portion and said second compliant portion are operable to couple said locking mechanism to said bone screw by deflecting said first compliant portion and said second compliant portion with said head of said bone screw to move said head through said aperture in said textured surface and into said accepting cavity in said body portion, and wherein said locking mechanism includes an aperture formed in said body portion of said first member in which said first and second compliant portions are disposed, wherein said aperture establishes an arcuate channel between a wall that defines said aperture and said first and second compliant portions to permit said first and second compliant portions to deflect and accept said head of said bone screw.

21. The knee implantation system of claim 20, wherein said first and second compliant portions each define a spherical contour that accepts said bone screw having said head with a spherical shape.

* * * * *

UNITED STATES PATENT AND TRADEMARK OFFICE
CERTIFICATE OF CORRECTION

PATENT NO. : 7,896,923 B2
APPLICATION NO. : 11/607109
DATED : March 1, 2011
INVENTOR(S) : Timothy J. Blackwell et al.

It is certified that error appears in the above-identified patent and that said Letters Patent is hereby corrected as shown below:

In the Claims

Column 11, Line 40, Claim 1; "an unicondyler" should be --a unicondyler--.

Column 12, Line 8, Claim 2; after "in", insert --a--.

Column 14, Line 21, Claim 12; "complaint" should be --compliant--.

Column 14, Line 37, Claim 14; after "in", insert --a--.

Column 15, Line 36, Claim 20; "an unicondyler" should be --a unicondyler--.

Column 16, Line 13, Claim 20; "complaint" should be --compliant--.

Signed and Sealed this
Twenty-fourth Day of September, 2013

Teresa Stanek Rea
*Deputy Director of the United States Patent and Trademark Office*